US007910065B2

(12) United States Patent
Clark

(10) Patent No.: US 7,910,065 B2
(45) Date of Patent: Mar. 22, 2011

(54) REACTION SENSING IN LIVING CELLS

(75) Inventor: Heather Clark, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 12/580,749

(22) Filed: Oct. 16, 2009

(65) Prior Publication Data
US 2010/0041067 A1 Feb. 18, 2010

Related U.S. Application Data

(62) Division of application No. 11/522,169, filed on Sep. 15, 2006.

(60) Provisional application No. 60/718,255, filed on Sep. 16, 2005.

(51) Int. Cl.
G01N 21/01 (2006.01)

(52) U.S. Cl. ...................... 422/82.06; 435/7.1

(58) Field of Classification Search .................. None
See application file for complete search history.

(56) References Cited

U.S. PATENT DOCUMENTS

| | | | |
|---|---|---|---|
| 4,272,484 A | 6/1981 | Lubbers | |
| 4,272,485 A | 6/1981 | Lubbers et al. | |
| 4,357,311 A | 11/1982 | Schutt | |
| 4,379,041 A | 4/1983 | Petranek et al. | |
| 4,945,171 A | 7/1990 | Haugland et al. | |
| 5,057,431 A | 10/1991 | Lubbers et al. | |
| 5,128,019 A | 7/1992 | Karpf et al. | |
| 5,132,095 A | 7/1992 | Koshiishi et al. | |
| 5,447,837 A | 9/1995 | Urnovitz | |
| 5,494,640 A | 2/1996 | Simon et al. | |
| 5,691,205 A | 11/1997 | Kawabata et al. | |
| 5,908,624 A * | 6/1999 | Scott et al. | 424/93.7 |
| 6,143,558 A | 11/2000 | Kopelman et al. | |
| 6,210,551 B1 * | 4/2001 | Osman et al. | 205/778 |
| 6,379,955 B1 | 4/2002 | Kopelman et al. | |
| 6,699,465 B2 * | 3/2004 | Scott | 424/78.08 |
| 2002/0155600 A1 | 10/2002 | Kopelman et al. | |
| 2003/0157535 A1 | 8/2003 | Berkovic | |
| 2003/0213691 A1 | 11/2003 | Peper et al. | |
| 2003/0217920 A1 | 11/2003 | Peper et al. | |
| 2004/0058384 A1 | 3/2004 | Bakker et al. | |
| 2004/0058458 A1 | 3/2004 | Anker et al. | |
| 2004/0146944 A1 | 7/2004 | Fang et al. | |
| 2005/0011760 A1 | 1/2005 | Bakker et al. | |
| 2006/0008924 A1 | 1/2006 | Anker et al. | |

FOREIGN PATENT DOCUMENTS

| | | |
|---|---|---|
| WO | WO-99/45357 | 9/1999 |
| WO | WO-01/08660 | 2/2001 |
| WO | WO-2004/083902 | 9/2004 |

OTHER PUBLICATIONS

Brasuel et al. (Anal Chem 2001 vol. 73, p. 2221-2228).*
Buck et al. (Talanta 2004 vol. 63, p. 41-59).*
Barker et al., "Radiometric and Flourescense-Lifetime-Based Biosensors Incorporating Cytochrome c' and the Detection of Extra- and Intracellular Macrophage Nitric Oxide," Anal. Chem., vol. 71, No. 9, May 1, 1999, pp. 1767-1772.
Buck et al., "Nanoscale Probes Encapsulated by Biologically Localized Embedding (PEBBLEs) for Ion Sensing and Imaging in Live Cells," Talanta, vol. 63, No. 1, May 10, 2004, pp. 41-59.
Bühlmann et al., "Carrier-Based Ion-Selective Electrodes and Bulk Optodes. 2. Ionophores for Potentiometric and Optical Sensors," Chem. Rev., vol. 98, Jan. 1, 1998, pp. 1593-1687.
Dubach et al., "Flourescent Ion-Selective Nanosensors for Intracellular Analysis with Improved Lifetime and Size," Nano Letters, vol. 7, No. 6, Jun. 2007, pp. 1827-1831.
Kohls et al., "Setup of a Fiber Optical Oxygen Multisensor-System and its Applications in Biotechnology," Sensors and Actuators B, vol. 70, (2000), pp. 121-130.
Sigworth et al., "Microchip Technology in Ion-Channel Research," IEEE Transactions on Nanobioscience, vol. 4, No. 1, Mar. 2005, pp. 121-127.
International Search Report for PCT Application No. PCT/US2006/036040, mailed Aug. 29, 2008, 4 pages, 2006.
Written Opinion for PCT Application No. PCT/US2006/036040, mailed Aug. 29, 2008, 7 pages.
European Search Report for European Patent Application No. 06 851 882.8, mailed Mar. 31, 2009, 5 pages.
Examination Report mailed Mar. 11, 2010 in European Patent Application No. 06851882.8 (5 pages).

* cited by examiner

Primary Examiner — Jacob Cheu
(74) Attorney, Agent, or Firm — Goodwin Procter LLP

(57) ABSTRACT

Chemical reactions occurring within a living cell are measured in a manner that does not affect the viability of the cell or the reaction under study. In one embodiment, one or more sensors are introduced into the cell and/or covalently associated with the exterior cell membrane. The sensor(s) emit an observable signal indicating a value of a parameter associated with the chemical reaction, e.g., the concentration of a reaction product. Because cell viability is not compromised, the cell may be stimulated (e.g., by subjection to an agonist or antagonist, a pathogen, a pharmaceutical compound, or a potential toxin) so as to affect the reaction under study.

20 Claims, 10 Drawing Sheets

REACTION SENSING IN LIVING CELLS

CROSS-REFERENCE TO RELATED CASES

This application is a divisional of U.S. patent application Ser. No. 11/522,169, filed Sep. 15, 2006, which claims the benefit of United States Provisional Patent Application No. 60/718,255, entitled "Optical Biosensor Array and Related Systems, Methods and Devices," filed on Sep. 16, 2005, the entire disclosure of each of which is hereby incorporated by reference as if set forth herein in its entirety.

FIELD OF THE INVENTION

The invention relates to monitoring chemical reactions occurring within living cells, and more particularly to methods and apparatus for measuring such reactions without compromising the viability of the cells.

BACKGROUND OF THE INVENTION

Numerous techniques exist for monitoring the extent and time profile of a chemical reaction of interest occurring within a living cell. Many such techniques are indirect, involving an assay for reaction products outside the cell that reflect the progress of reaction(s) taking place in the cytoplasm. A disadvantage of such assays is their vulnerability to influence by the spurious presence of reaction products in the cell's environment that do not, in fact, emanate from the cell.

Intracellular techniques have also been developed; these include, for example, genetically engineering cells to fluoresce in the presence of a compound of interest, radioactive binding assays, and colorimetric assays. These techniques, however, require potentially destructive modification or invasion of the cell.

Intracellular and extracellular assays are often employed to track enzymatic activity by measuring the amount of reaction product through the use of coupling. Enzymatic coupling is a complicated approach that links a non-quantifiable enzymatic reaction of interest with an optically measurable (by means of a spectrophotometer) enzymatic reaction that will interact with the products of the enzymatic reaction of interest. Once again, conventional approaches suffer from a number of deficiencies. For example, coupled reactions necessarily involve at least one chemical reaction unrelated ("coupled") to the enzymatic activity of interest, imparting potential sources of error. Enzymatic reactions require carefully controlled reaction conditions (appropriate temperatures, pHs, salt concentrations, etc.) and, as a result, monitoring efforts can be affected by rapid environmental changes or degradation of reagents, e.g., components of the enzymatic reactions (especially the enzyme itself).

Accordingly, there is a need for apparatus and methods that quickly, directly and accurately measure a product of interest.

SUMMARY OF THE INVENTION

The present invention addresses the shortcomings of the prior art by measuring chemical reactions occurring within a living cell in a manner that does not significantly affect the viability of the cell or the reaction under study. By "significantly" is meant, with respect to individual cells, that these are not killed; with respect to a population of cells, that at least the majority remains viable; and with respect to a reaction, that the variable under study is not affected beyond a predetermined threshold of precision. For example, if it is necessary to monitor the concentration of an ion to within 0.1 mole/L, the reaction is not significantly affected if the ion concentration is not shifted more than ±0.05 mole/L.

In one embodiment, one or more sensors are introduced into the cell and/or covalently associated with the exterior cell membrane. The sensor(s) produce an observable signal indicating a value of a parameter associated with the chemical reaction, e.g., the concentration of a reaction product. Because cell viability is not compromised, the cell may be stimulated (e.g., by subjection to an agonist or antagonist, a pathogen, a pharmaceutical compound, or a potential toxin) so as to affect the reaction under study. By "observable" is meant visible or measurable using instrumentation.

In some embodiments, the sensor is used to monitor the activity of an ion channel through the cell membrane. In such cases, the sensor may be introduced within the cell, may be attached to the exterior cell membrane, or both. For example, the external sensor may be attached to the cell membrane proximate to an ion channel of the cell, e.g., via an antibody specific to the ion channel (which typically comprises a protein). The sensor may be an ion sensor, and sensors internal and external to the cell may monitor different ions.

In some embodiments, the sensor comprises an ion-selective optode. The reaction may produce an ionic product that is sequestered by the optode, or instead, the reaction may produce a non-ionic product that is ionized to facilitate monitoring using the optode. In this way, the invention can be used in numerous pharmaceutical applications involving small molecules.

In some embodiments, the optode comprises an ion-selective ionophore, a source of triggering ions, and a signaling agent responsive to the triggering ions. Typically the ionophore is selective for the ionic reaction product, and upon binding of a reaction-product ion, a triggering ion is released to interact with the signaling agent and thereby produce the signal. The strength of the signal may be indicative of the concentration of the triggering ion, which itself reflects the concentration of the ionic reaction product. Different sensors, each responsive to different ions and producing differentiable signals, can be used depending on the reaction(s) being monitored. Furthermore, the signal may be produced directly by the triggering ions, or may be produced indirectly (e.g., the triggering ions may initiate a reaction cascade that results in an observable signal).

In preferred embodiments, the signal is optical in nature, e.g., involving fluorescence or absorbence. The optical signal may be monitored using, for example, a spectrometer, a flurometer, or a detector for measuring absorbance. But the signal may alternatively be non-visible or may involve other forms of electromagnetic radiation.

The foregoing and other features and advantages of the present invention will be made more apparent from the description, drawings, and claims that follow.

BRIEF DESCRIPTION OF DRAWINGS

The advantages of the invention may be better understood by referring to the following drawings taken in conjunction with the accompanying description in which.

In the drawings, like reference characters generally refer to corresponding parts throughout the different views. The drawings are not necessarily to scale, emphasis instead being placed on the principles and concepts of the invention.

DETAILED DESCRIPTION OF THE INVENTION

In brief overview, embodiments of the present invention provide systems, methods and devices for measuring cellular biomarkers. In exemplary embodiments, optically active polymer sensors are placed inside or outside a cell. Changes in fluorescence or absorbance indicate the ion concentrations and fluxes from the cell. The overall change in fluorescence or absorbance in response to a compound of interest provides a "fingerprint" (e.g., a spectrum) for that compound.

Figure 1:
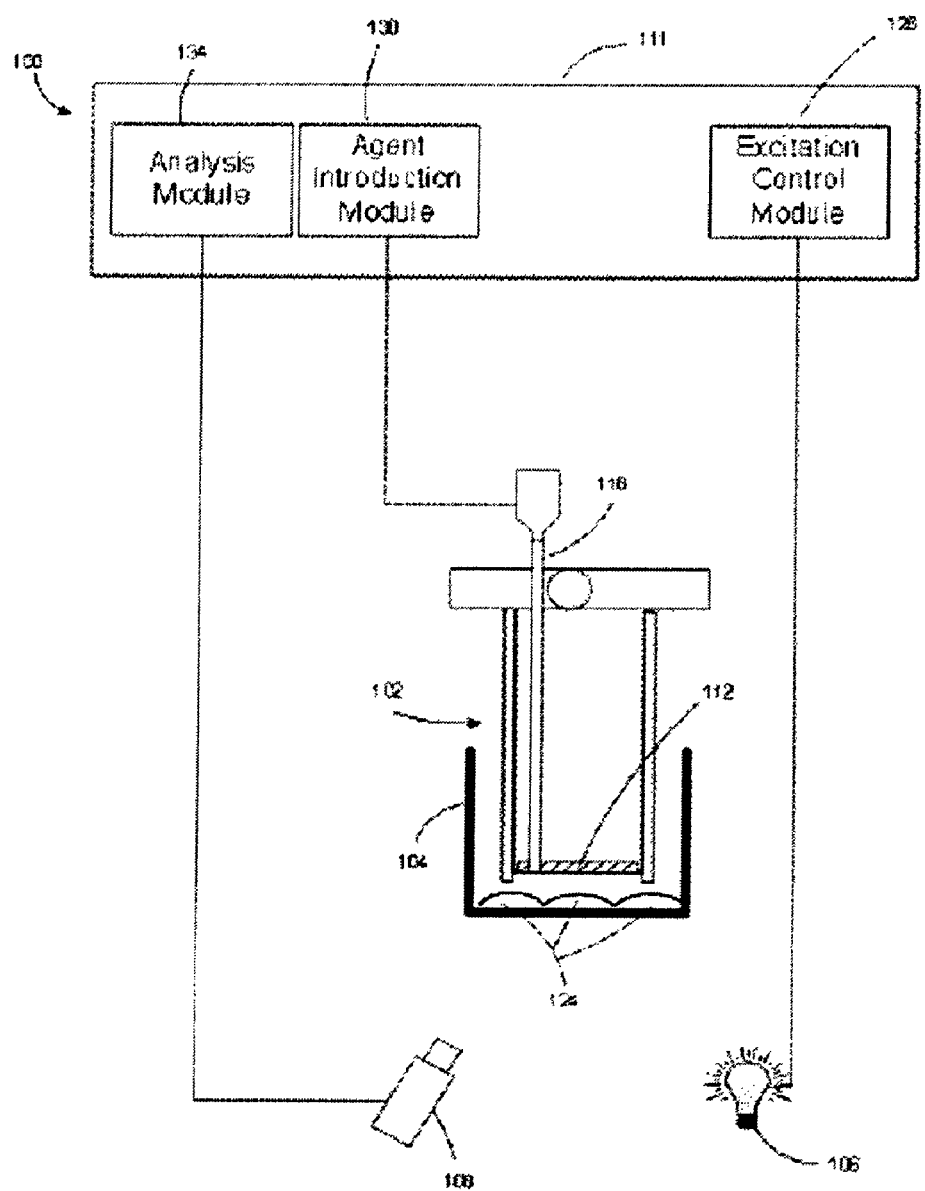
FIG. 1 is a schematic diagram of a cell assay system according to an illustrative embodiment of the invention.

FIG. 1 is a schematic diagram of a cell assay system 100 according to an illustrative embodiment of the invention. The cell assay system 100 includes an optical ion sensor support 102, a biological sample holder 104, an excitation light source 106, a light sensor 108, and a computing device 111.

The optical ion sensor support 102 supports an optical ion sensor 112 for positioning in the biological sample holder 104. In various implementations, the optical ion sensor 112 is adhered to the optical ion sensor support 102 by deposition in a solution of optical ion sensor matrices dissolved or dispersed in a solvent, such as in a polar organic solvent like tetrahydrofuran (THF). In such implementations, the sensor support 102 is preferably formed from a material resistant to the solvent. Materials resistant to THF include, without limitation, 304 stainless steel; 316 stainless steel; acetal polymer (marketed as DELRIN by E. I. du Pont de Nemours and Company); bronze; carbon graphite; carbon steel; ceramic $Al_2O_3$; a perfluoroelastomer compound, such as CHEMRAZ marketed by Greene, Tweed; epoxy; HOSTELRY Calloy (marketed by Haynes International, Inc.); KALES elastomer (marketed by DuPont Performance Elastomers); polychlorotrifluoroethylene; NYLON (marketed by E. I. du Pont de Nemours and Company); polyetherether ketone (PEEK); polyphenylene sulfide; and PTFE.

The optical ion sensor 112 includes a film having a suspension of optical ion sensor matrices. The optical ion sensor matrices, in general, include an ionophore, an additive, and a chromionophore suspended in a polymer phase, for example, of polyvinyl chloride (PVC). The polymer phase also includes a plasticizer such as dioctyl sebacate (DOS). An ionophore is a substance that allows targeted ions to move across or into a membrane. Preferably the ionophore is selected to be lipid-soluble. In addition, the ionophore is preferably an electrically neutral compound that forms a complex with a target ion. The ionophore is optically inactive in the visible spectrum and does not change absorbance or fluorescence depending on its state of complexation.

A chromoionophore is an ionophore that changes its optical properties in the visible spectrum depending on the state of complexation. Chromoionophores are preferably proton-sensitive dyes that change absorbance (and fluorescence in many cases) depending on its degree of hydrogen complexation (protonation). The chrominonophores are preferably highly lipophilic to prevent them from leaching out of the optical ion-sensor matrix. Suitable chrominonophores include Chromoionophore II and Chromionophore III. Chromoionophore II exhibits light absorbance peaks at 520 nm and 660 nm and a fluorescent emission peak at 660 nm. Chromoionophore III has light absorbance peaks at 500 nm and 650 nm and fluorescent emission peaks at 570 nm and 670 nm.

It should be stressed that the triggering ion released by the ionophore may be observed directly, as discussed above, or indirectly. For example, the intensity of the fluorescence signal may be a trigger for an event cascade within the cell. A large calcium current may cause the sensor to fluoresce brightly, for instance, whereas low calcium does not. The fluorescence may in turn excite a secondary dye in the particle that easily generates reactive oxygen species (ROS). The ROS would then attack the cell, effectively stimulating necrosis (cell death). Alternatively, instead of a secondary component within the particle, another particle may be added. This additional particle may comprise a photo-degradable polymer. When the primary sensory fluoresces, the emitted light will break apart the secondary particle, releasing its contents. The contents may, for example, be a drug that is therapeutic or cancer-fighting (stimulating apoptosis).

For optical ion sensors targeting cations, the additive can be any inert lipophilic component that has a negative charge associated with it. For optical ion sensors targeting anions, the additive is positively charged. The purpose of the additive is to embed charge sites within the polymer phase, and to help enforce charge neutrality within the optical ion sensor 112. The additive allows the polymer phase to carry an equal amount of charged particles as additive. The concentration ratio of additive to chromoionophore is preferably 1:1, thereby allowing the chromoionphore to become completely protonated or de-protonated. One suitable additive for optical ion sensors targeting negative ions is potassium tetrakis[3,5-bis(trifluoromethyl)phenyl]borate (KTFPB). The lipophilic, anionic component TFPB molecules are retained by the polymer phase, and the potassium ions are either complexed by the ionophore or expelled into the sample solution through diffusion. In one particular implementation, the optical ion sensor film is composed of a suspension produced from about 60 mg of DOS, 30 mg of PVC, and up to about 5 mg of additive, ionophore, and chromionophore.

Once the above components are dissolved into the polymer phase to form the optical ion sensor 112 and are exposed to a sample solution, the optical ion sensor 112 becomes active. It now continuously extracts or expels analyte cations (a system can work with anions as well using ion coextraction) depending on ion activity in the sample solution. With a 1:1 additive-chromoionophore ratio, and with zero target ions present in the sample solution, the optical ion sensor 112 remains completely protonated to achieve charge neutrality. As the target ion concentration increases, the ionophores in the optical ion sensor 112 extract the target ions into the optical ion sensor 112. To maintain charge neutrality of the optical ion sensor 112, hydrogen (hydronium) ions are stripped from the chromoionophores in the optical ion sensor 112 and expelled into the sample solution. The expelling of hydrogen ions alters the pH of the optical ion sensor 112, thereby altering its fluorescent properties. To detect analyte anions (for example, chloride or nitrite ions), the optical ion sensor uses ion-coextraction, as opposed to proton expulsion. To detect neutral analytes, an additional agent known to interact with the target analyte to yield an ion is added to the biological sample holder 104. An ionophore is then selected to detect the resultant ion.

The following is a non-limiting, illustrative list of target ion/ionophore pairings suitable for use in the optical ion sensors: potassium/Potassium Ionophore III (BME-44), sodium/Sodium Ionophore IV, sodium/Sodium Ionophore V, sodium/Sodium Ionophore VI, calcium/Calcium Ionophore III, and calcium/Calcium ionophore IV. For target anions, illustrative target ion/ionophore pairings include chloride/Chloride Ionophore III and nitrite/Nitrite Ionophore I.

The film of the optical ion sensor can be produced in various ways. In one implementation, as described above, a predetermined amount of the optical ion sensor suspension (i.e., the combined polymer phase, ionophore, additive, and chromionophore) is dissolved in a solvent, such as THF. The solution is then deposited, sprayed, or spun onto a surface. The solvent evaporates, leaving the optical ion sensor film on the surface.

In another implementation, the film is formed from a deposition of optical ion sensor microspheres. To produce the microspheres, an optical ion sensor emulsion is formed by injecting an optical ion sensor suspension dissolved in THF (e.g., 16 mL THF/100 mg PVC) into a pH buffered solution. The optical ion sensor suspension includes approximately 60 mg of DOS, 30 mg of PVC, and up to approximately 5 mg of chromionophore, additive, and ionophore. The emulsion is then submerged in a sonicating water bath. Typically, 50 μL of the optical ion sensor suspension/THF solution is injected into 1,000-1,500 μL of buffered solution. The resulting emulsion contains a mixture of spherical optical ion sensor particles ranging in size from 200 nm to 20 μm. The resulting emulsion can be spun, sprayed, or evaporated onto any surface to create a porous optical ion sensor membrane. Films formed from microspheres tend to expose a greater surface area of optical ion sensor to a given sample, yielding improved performance characteristics.

The biological sample holder 104 holds a biological sample for analysis by the cell assay system 100. The biological sample can include cells adhered to the walls of the biological sample holder 104, for example, in a monolayer, or cells suspended in a liquid buffer. The biological sample holder 104 is preferably transparent, or at least includes a transparent region through which the optical ion sensor 112 can be excited and through which the results of such excitement can be monitored.

The optical ion sensor 112 is illuminated with a light source 106 to excite the chromionophores suspended therein. The light source preferably can be tuned to generate one or more predetermined wavelengths of light, desirably in the visible portion of the electromagnetic spectrum, that are selected to excite the particular chromionophore used in the optical ion sensor 112. Alternatively, the light source may generate a wide spectrum light. In one implementation, the light source 106 is coupled to the optical ion sensor support 102.

The fluorescence of the optical ion sensor 112 is detected by a light sensor 108. The light sensor 108 may include a charge-coupled device, a fluorometer, a photomultiplier tube, or other suitable device for measuring fluorescence. In one implementation, a spectrophotofluorometer is used to satisfy the roles of the light source 106 and the light sensor 108. The light sensor 108 may also be coupled to the optical ion sensor support 102.

The optical ion sensor support 102 includes an agent introduction means 118. The agent introduction means 118 can include a pipette or an electromechanical dispenser device, such as a solenoid or electrostatically driven plunger or syringe.

The computing device 111 controls the various components of the cell assay system 100. The computing device 111 may be a single computing device or multiple computing devices providing the various functionalities used to control the cell assay system. These functionalities are provided by an excitation control module 126, an agent introduction module 130, and an analysis module 134. The excitation control module 126 controls the light source 108 to emit one or wavelengths of excitation light. The agent introduction module 130 controls the introduction of an agent into the biological sample holder 104 via an agent introduction means 118. The analysis module 134 analyzes the output of the light sensor 108, e.g., before and after an agent is introduced into the biological sample holder 104 to determine the effect of the agent on the cells in the biological sample holder 104. The analysis module 134 may also control the other modules in the computing device, i.e., the excitation control module 126 and the agent introduction module 130, to coordinate an assay protocol. The computing device 111 and/or devices may also include various user interface components, such as a keyboard, mouse, trackball, printer, and display.

A module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module. A module of executable code may be a single instruction, or many instructions, and may even be distributed over several different code segments, among different programs, and across several memory devices.

The various modules are in communication with the various devices they control or obtain data from. They maybe connected over a local area network, wirelessly, over a bus, or over typical cables known in the art of computer interfaces for connecting computing devices with peripherals.

Figure 2A:
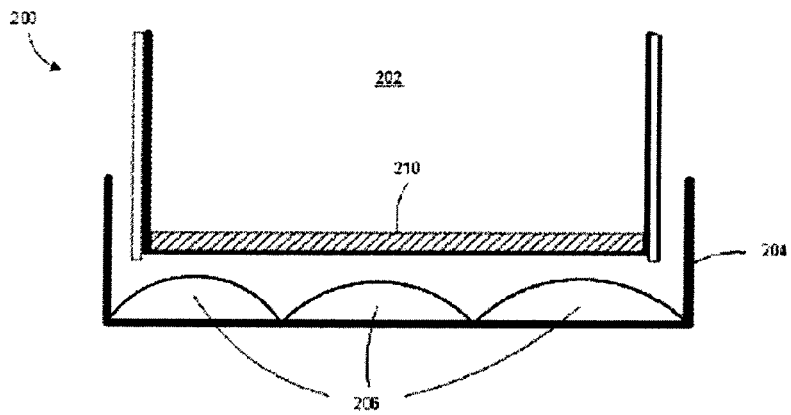
FIGS. 2A-2D are cross-sections of various optical ion sensor arrangements suitable for use in various implementations of the cell assay system of FIG. 1.

FIGS. 2A-2D depict various optical ion sensor arrangements suitable for use in various implementations of the cell assay system 100 of FIG. 1. FIG. 2A shows a first optical ion sensor arrangement that includes an optical ion sensor support 202 and a biological sample holder 204. The biological sample holder 204 includes a monolayer of cells 206 adhered to the biological sample holder 204. Alternatively, the biological sample holder 204 holds cells suspended in a buffer. The optical ion sensor support 202 and biological sample holder 204 correspond to the optical ion sensor support 102 and biological sample holder 104 of FIG. 1. An optical ion sensor film 210 is coupled to the distal end of the optical ion sensor support 202.

Figure 2B:
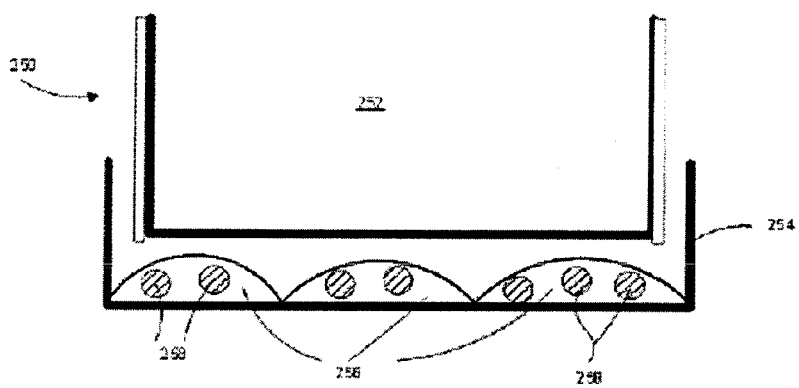

FIG. 2B illustrates an alternative optical ion sensor arrangement 250, which includes a biological sample holder 254 having therein a monolayer of cells 256 adhered to the surfaces of the biological sample holder 254, or cells suspended in a buffer. Instead of including an optical ion sensor film adhered to a support, the optical ion sensor arrangement 250 relies upon optical ion sensor particles 258 introduced into the cells 256 adhered to the biological sample holder 254.

To introduce optical ion sensors into cells, the optical ion sensors are produced as particles 258. The optical ion sensor particles 258 are fabricated in a fashion similar to the optical ion sensor film 112 described above. One such particle 258, the optical ion sensor nanosphere, is produced according to the following procedure. First a optical ion sensor suspension is dissolved in 500 µl of THF. The suspension preferably includes 60 mg of DOS, 30 mg of PVC and up to about 5 mg of chromoionophore, ionophore, and additive to form an optode solution. Then, 500 µl of CH2Cl2 is added to bring the total volume to 1 ml. Next, a PEG-lipid solution is prepared by dissolving a PEG-lipid (such as DSPE-PEG 550 or DSPE-PEG (2000) Folate) in 5 ml of a water, salt and buffer solution. A TAT peptide can be added to the PEG-lipid via an amine linkage to aid the resulting nanospheres in entering cells. Alternatively, it is possible to utilize a molecule that is not a PEG, e.g., a ganglioside attached to ceramide.

The nanospheres are formed by adding 100 µl of optode solution dropwise to 5 ml of the PEG-lipid solution while the solution is being sonicated by a probe tip sonicator. Additional sonication is performed for approximately 2-3 minutes. The resultant nanosphere solution is sprayed through a nitrogen-feed air gun into a beaker several times to remove excess solvent. If desired, the nanosphere solution is pushed through a 0.22 µm filter to remove the larger spheres.

The optical ion sensor particles 258 are introduced into the cells 256 in any suitable manner. In one method, the particles 258 are introduced into a buffer liquid deposited in the biological sample holder 254. A voltage source then generates a voltage sufficiently strong to electroporate the cells 256, thereby allowing the optical ion sensor particles 258 to enter directly into the cells. In another approach, the surfaces of the optical ion sensor particles 258 are first coated with a substance, for example transferrin or folate, which assist the particles 258 in crossing through cell membranes. The optical ion sensor particles 258 are introduced into a buffer in the biological sample holder 254, and the cells 256 bring the particles 258 into their interior in vesicles via endocytosis, pinocytosis, or phagocytosis, or similar biological processes. The substance applied to the optical ion sensor particles 258 breaks down the vesicle membrane, releasing the optical ion sensor particles 258 into the cell cytoplasm. In still other approaches, the particles 258 may be introduced into cells 256 using a glass needle or through ballistic bombardment.

In some embodiments, the sensor is attached to the exterior of a cell rather than introduced into the interior. If, for example, the activity of an ion channel is to be studied, the sensor may be attached to the cell proximate to the ion channel. This may be accomplished, for example, by raising antibodies against the ion-channel protein and, using conventional chemistries, covalently linking one or more such antibodies to a sensor particle as described above. The antibody-studded particles are released into a cell suspension and preferentially bind to the ion channel. This approach can be used to link ion-specific sensors to any feature on the exterior of the cell membrane to which antibodies can be raised.

Alternatively, the sensors may be attached to the cell membrane by other suitable coupling chemistries, e.g., biotin-(strept)avidin complexing or polysaccharide binding. See the thesis "High Throughput Optical Sensor Arrays for Drug Screening" by Daniel I. Harjes (2006), available from the Massachusetts Institute of Technology and incorporated herein by reference.

Figure 2C:
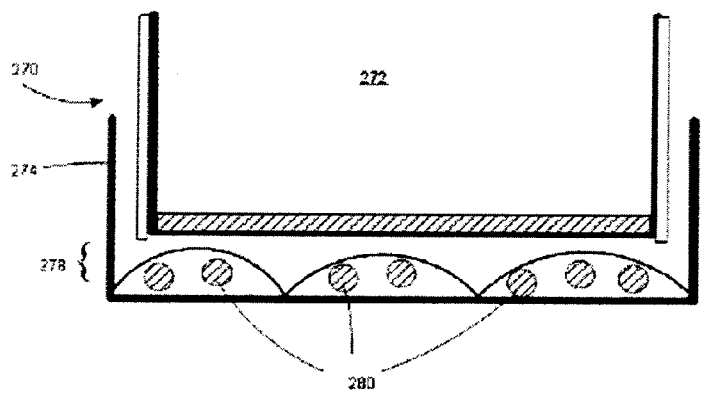

FIG. 2C illustrates a second alternative optical ion sensor arrangement 270 that includes an optical ion sensor support 272 and a biological sample holder 274. An optical ion sensor film 276 is coupled to the distal end of the optical ion sensor support 272. A cell monolayer 278 adheres to the surfaces of the biological sample holder 274. Alternatively, cells are suspended in a buffer. In addition, optical ion sensor particles 280 are introduced into the cells of the cell monolayer 278. Preferably the chromionophores used in the optical ion sensor film 276 differ from the chromionophores used in the optical ion sensor particles 280. In particular, the different chromionophores desirably have distinguishable fluorescence characteristics such that an analysis module analyzing the output of a light sensor monitoring the optical ion sensor arrangement 270 can differentiate between the output of the optical ion sensor film 272 and the optical ion sensor particles 280. As a result, the analysis module can differentiate between intracellular target ion concentration and extracellular target ion concentration. In addition, the optical ion sensor film 272 may include ionophores different from those included in the optical ion sensor particles 280. Thus, the optical ion sensor arrangement 270 can monitor the concentrations of two different target ions.

Figure 2D:
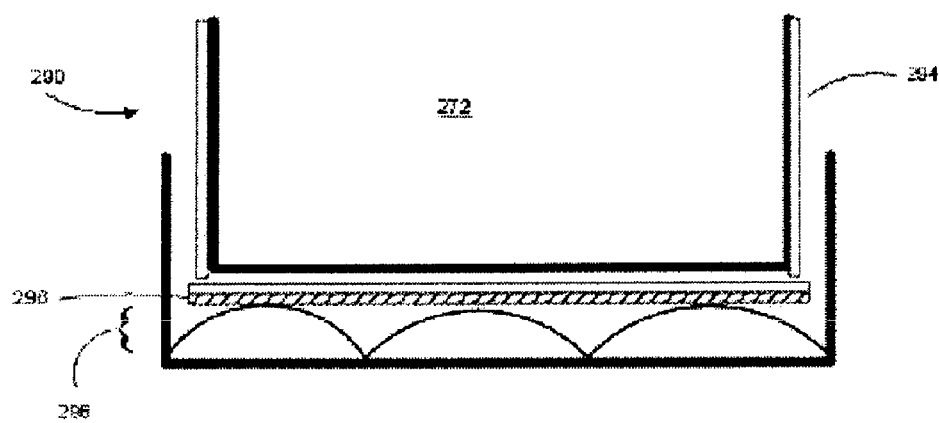

FIG. 2D illustrates a third alternative optical ion sensor arrangement 290 that includes an electrode support 292 and a biological sample holder 294. The biological sample holder 294, in addition to a cell monolayer 296 or cells suspended in a buffer, includes a removable optical ion sensor film 298. The removable optical ion sensor film 298, for example, can be a glass cover slip or other transparent surface coated with an optical ion sensor film.

In still another embodiment, the optical ion sensor film is coated onto the inner surface of the biological sample holder. And in another approach, to accommodate the 96-well plate format often used in assays, one embodiment of the present invention utilizes round glass coverslips coated with the ion-exchange optode material along with the cells to be monitored. In this embodiment, each well contains a single sensor type to track a specific species of interest; the various sensor types may differ only in the ionophore employed and utilize the same or similar chromoionophores. The compound of interest is then added directly to the well. The 96-well plate is then placed in a standard plate-reader type fluorometer, and the fluorescence intensity is monitored with time.

In a typical implementation, a plurality of biological sample holders holding biological samples is provided. Biological samples introduced into the holders may include cells suspended in a buffer solution, but alternatively, cells may be adhered to the walls of the biological sample holders. Next, optical ion sensors are introduced into the biological sample holders as shown in FIGS. 2A and 2C, and/or are introduced into the cells themselves. Alternatively, the optical ion sensors can coat the walls of the biological sample holders. As described above, optical ion sensor particles can be introduced either by electroporating the cells via electrodes positioned in the biological sample holders or by the chemistry applied to the optical ion sensor particles breaching vesicle membranes within the cells. Similarly, the optical ion sensor sensors can be introduced into the cells using pico-injection, bead loading, a gene gun, or through liposomal delivery techniques known in the art. As described above, the optical ion sensors include at least one ionophore for selectively binding a predetermined ion. In some embodiments, this results in altering the pH of the optical ion sensor and a pH-sensitive chromionophore for optically indicating the concentration of the ion in a fluid surrounding the optical ion sensor. Ion concentration, in other words, is indicated by the pH of the optical ion sensor and the resulting fluorescence of the chromionophore.

An agent, such as a therapeutic, toxin, biological macromolecule (such as a nucleic acid, an antibody, a protein or portion thereof, e.g., a peptide), small molecule (of 2000 amu or less, 1000 amu or less or 500 amu or less), protein, virus, bacteria, chemical compound, mixture of chemical compounds, or an extract made from biological materials such as bacteria, plants, fungi, or animal (particularly mammalian) cells or tissues, or other biologically active agent may be introduced into one or more of the biological sample holders. In one particular implementation using an array of biological sample holders, no agent is introduced into a first row of biological sample holders to preserve a control. A first agent is introduced into a second row of biological sample holders. Additional agents are added to additional rows of the array of biological sample holders.

The fluorescence of the optical ion sensors introduced into the biological sample holders is monitored. The monitoring preferably begins prior to introduction of the agents and continues thereafter. Changes in ion concentration resulting from the introduced agents are then determined. By comparing the changes in ion concentration after adding an agent, one can determine the effect of the agent on the cells being tested.

Figure 4:
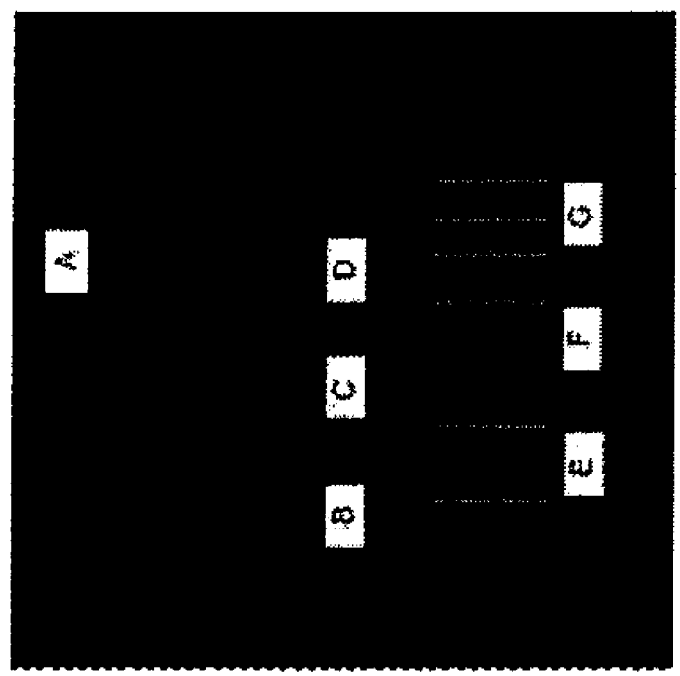
FIG. 4 depicts the embodiment of FIG. 5 with fluorescence from the channels imaged.
Figure 3:
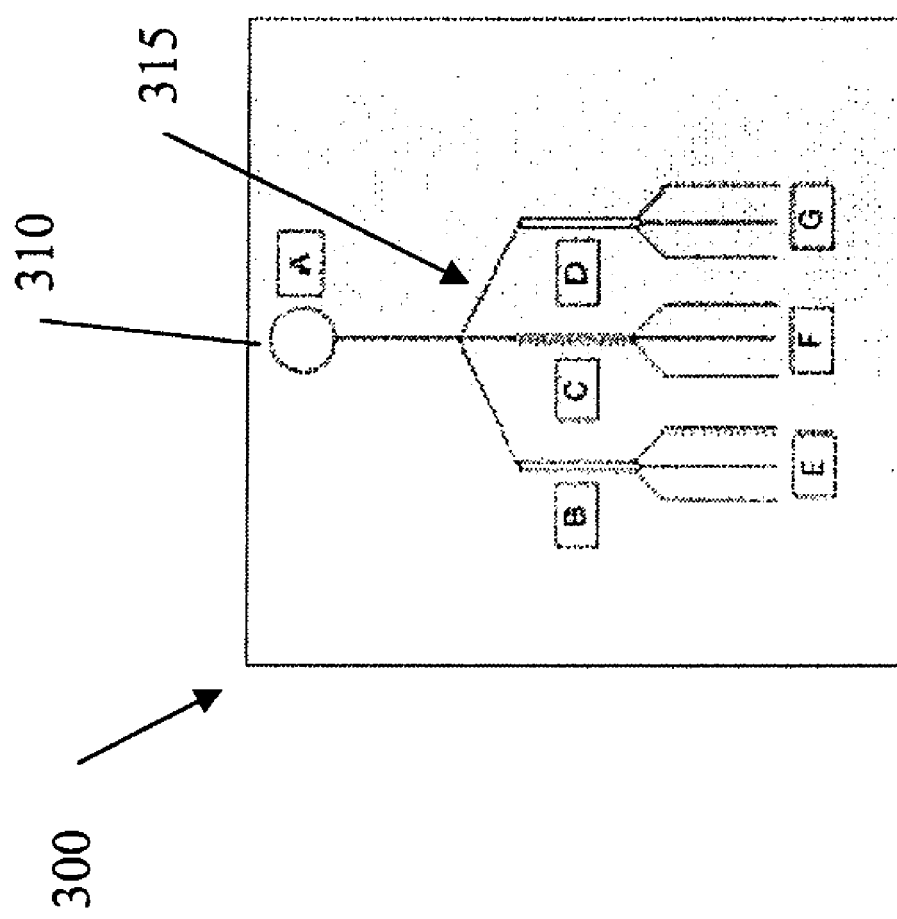
FIG. 3 presents another embodiment of a microfluidic device in accord with the present invention.

FIGS. 3 and 4 present another embodiment 300 of a sensor in accord with the present invention. The sensor comprises a well 310 and micro-channels, indicated generally at 315, branching successively therefrom. The cells are placed in the well 310, sensor materials with different specificities line each of the channels 315, and a solution is flowed from the well 310 through the channels 315. When the fluorescence from the channels 315 is imaged, the pattern formed by changes in intensity may be visualized as an optical barcode, as depicted in FIG. 4, indicating the presence or absence of the various sensed materials in the solution.

Exemplary Applications: HERG Compatibility

The sensors of the present invention are suited to many different types of assays, or for the detection of compounds. In one exemplary application, a model cell system is used to screen for HERG compatibility. HERG (human ether-a-go-go) channels are implicated in the abnormal heart rhythms associated with Long QT Syndrome. It is believed that many compounds can block these channels and cause prolongation of the beat cycle of the heart. This abnormal rhythm can cause arrhythmia and can even lead to death. Accordingly, it is important that all drugs, regardless of therapeutic target, be screened for HERG compatibility.

Figure 5:
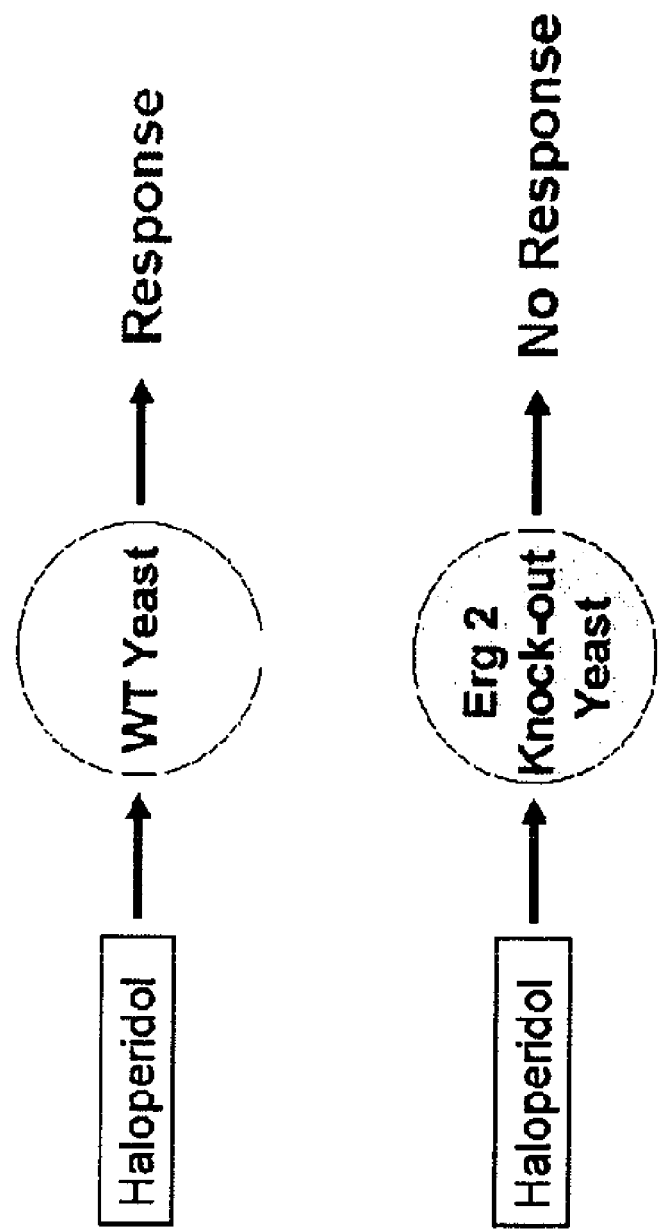
FIG. 5 presents a hypothetical response of yeast cells to a stimulus (Haloperidol).

With reference to FIG. 5, the model cell system to be used is *Saccharomyces cerevisae*, as it contains a native ERG2 gene which is similar to the human HERG. It has been shown that known HERG inhibitors also interfere with the function of ERG2 in yeast. Much is known genetically about yeast, and gene knock-outs are commercially available, allowing for the screening of two types of yeast: the wild type (WT) containing the ERG2, and one mutated to knock-out the ERG2 gene.

Figure 6:
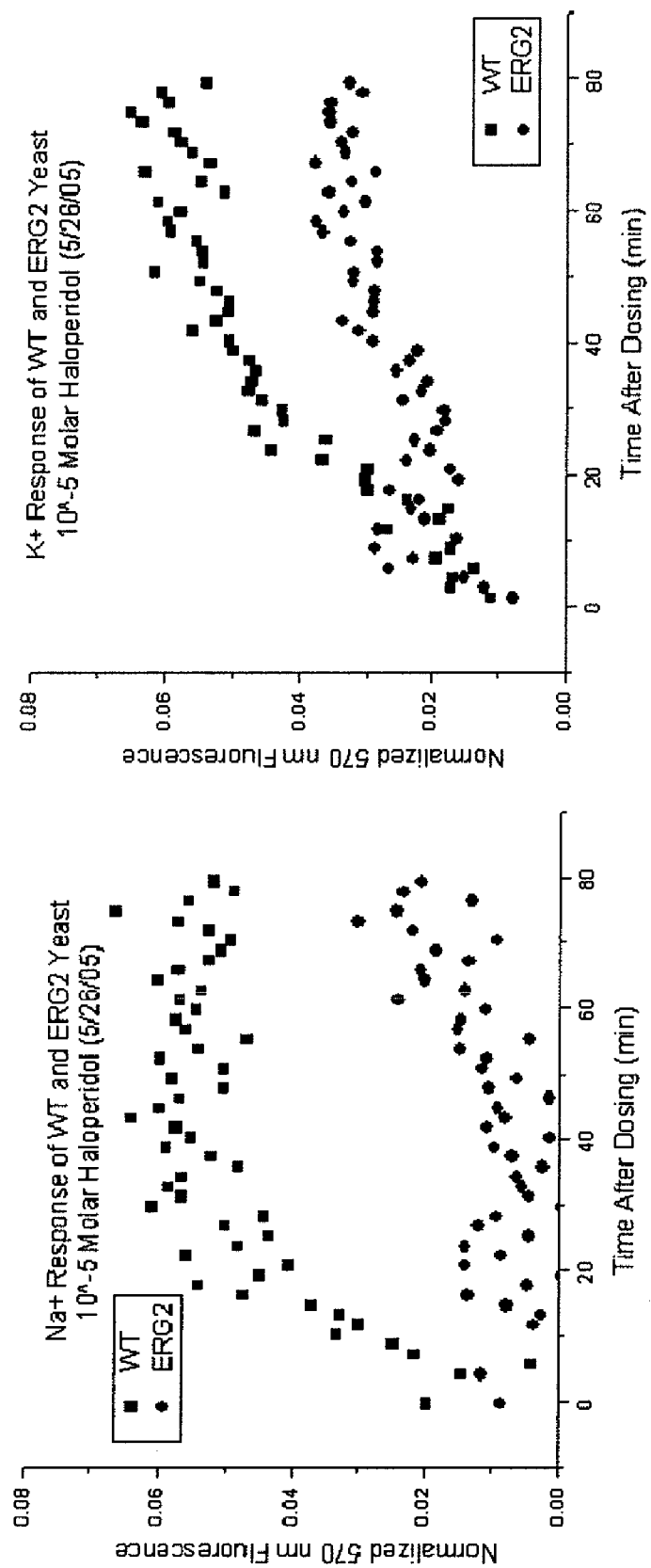
FIG. 6 presents data from an exemplary study using a sensor in accord with the present invention to monitor the reaction of yeast cells to Haloperidol. Sodium is shown on the left and potassium on the right.

With reference to FIG. 6, using both potassium and sodium sensors according to the present invention with both yeasts stimulated with a known HERG inhibitor, Haloperidol (an anti-psychotic drug), a change is observed in sodium and potassium upon stimulation of the cells with Haloperidol. In the ERG2 knock-out, there is no response. This example utilizes two cell types and two types of sensors, providing four different data signals, and the approach can be extended to an arbitrary number of sensors and cell types. Similarly, tissue can be used instead of culture.

Exemplary Applications: Ammonia Screening

As explained above, pH changes can be used to render neutral reaction products of interest measurable using an ion-exchange optode. For a sensor developed to monitor ammonia production in biological reactions (e.g., involving an enzyme such as transglutaminase (TGase)), for example, a low pH ionizes ammonia to ammonium, which may be extracted by a nonactin ionophore. This approach greatly expands the range of measurable species.

Figure 7:
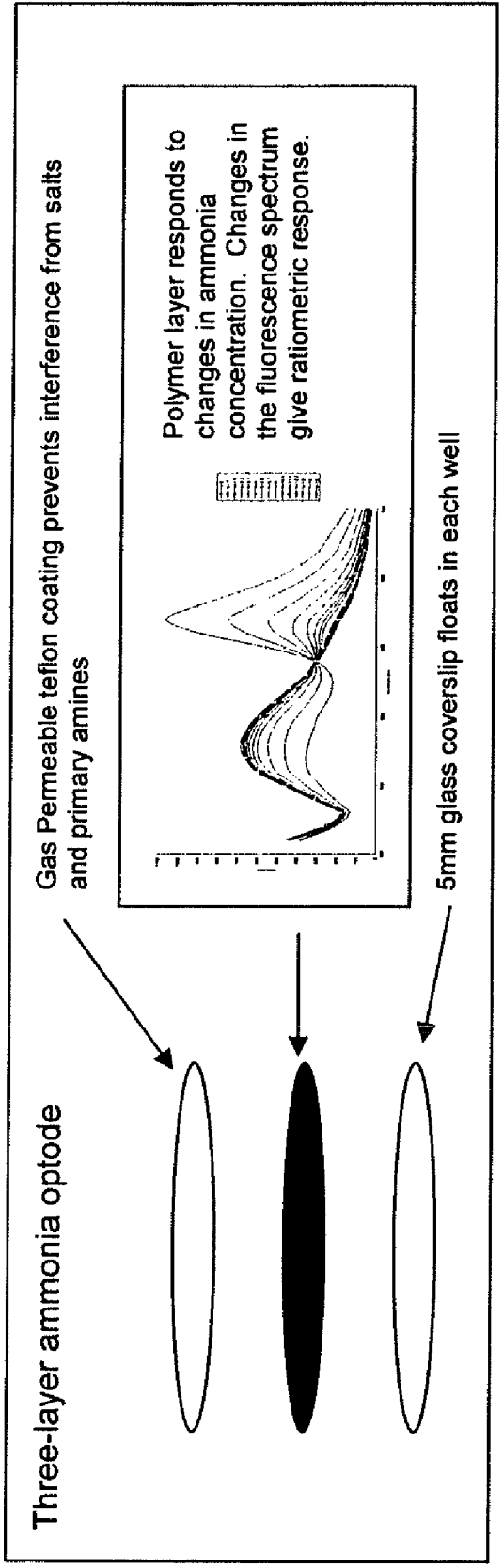
FIG. 7 illustrates an embodiment of the present invention used as an ammonia sensor.

With reference to FIG. 7, an ammonia sensor is made by coating a 5 mm glass disk with an ammonium/ammonia-selective cocktail containing PVC, plasticizer, THF, potassium tetrakis (p-chlorophenyl)borate (KTpClPB), Chromoionophore III, and nonactin. A second, thin layer of 5% TEFLON is optionally applied to the coated disk to protect the ammonium cocktail from the high-salt environment required for the enzymatic reaction. These disks are placed in the bottom of individual wells in 96-well plates and the enzymatic reaction is set up to occur in the well, submerging the disks. Real-time monitoring of the reaction (through measuring the change in fluorescence of the optical sensor) is performed. Although these optodes are fairly large and coated with TEFLON, their response time is still approximately 2 minutes.

Figure 8:
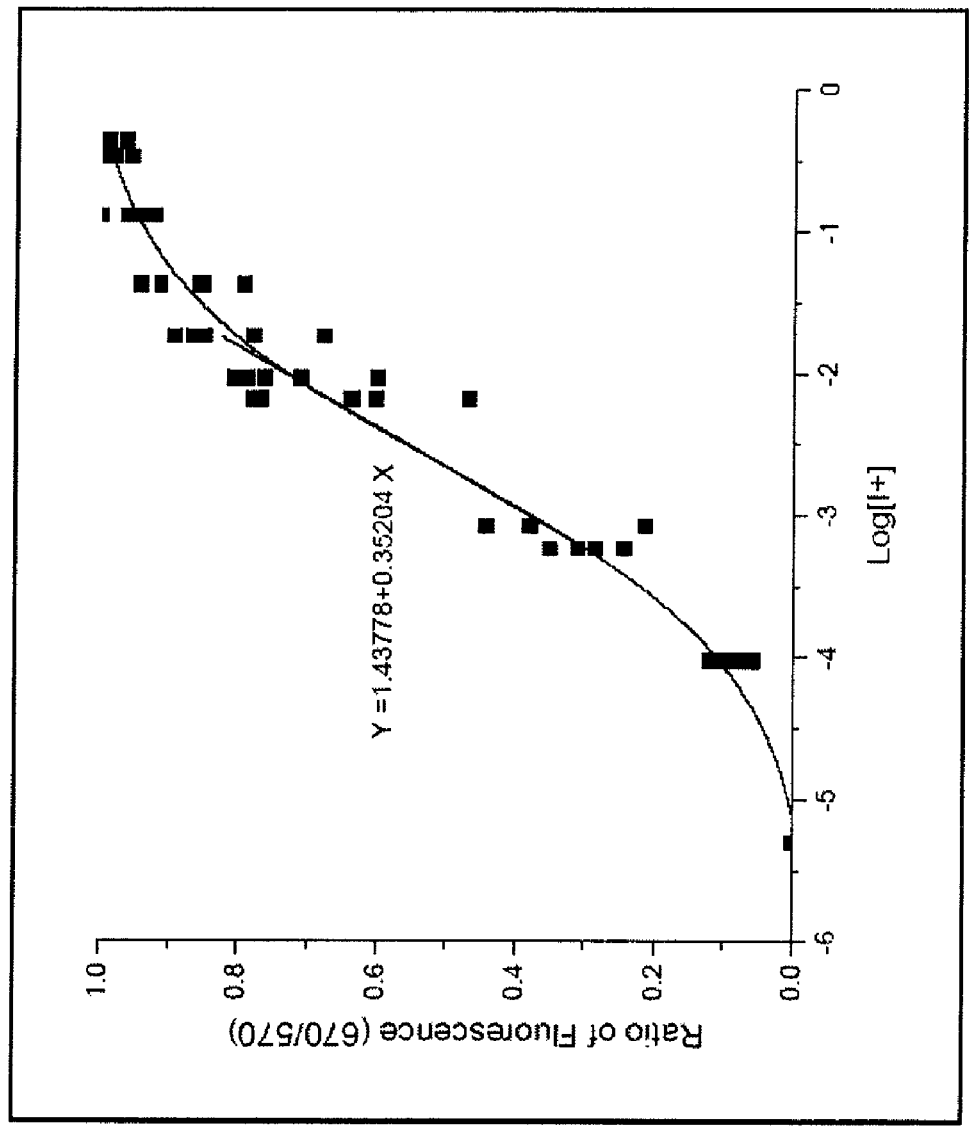
FIG. 8 depicts the calibration curve for the embodiment of FIG. 7.

To utilize data monitoring in order to track the change in fluorescence of the sensors in the presence of an enzymatic reaction, a calibration curve of fluorescence readings of known concentrations of the ion of interest is first constructed. With reference to FIG. 8, this curve is typically sigmoidal, with the linear portion of the curve coinciding with the sensor's range of greatest accuracy. As depicted, in the case of a TGase reaction, the ammonia concentration currently susceptible to measurement is $10^{-4}$-$10^{-3}$ M, although sensitivity is anticipated in the range of $10^{-5}$-$10^{-3}$ M.

Figure 9:
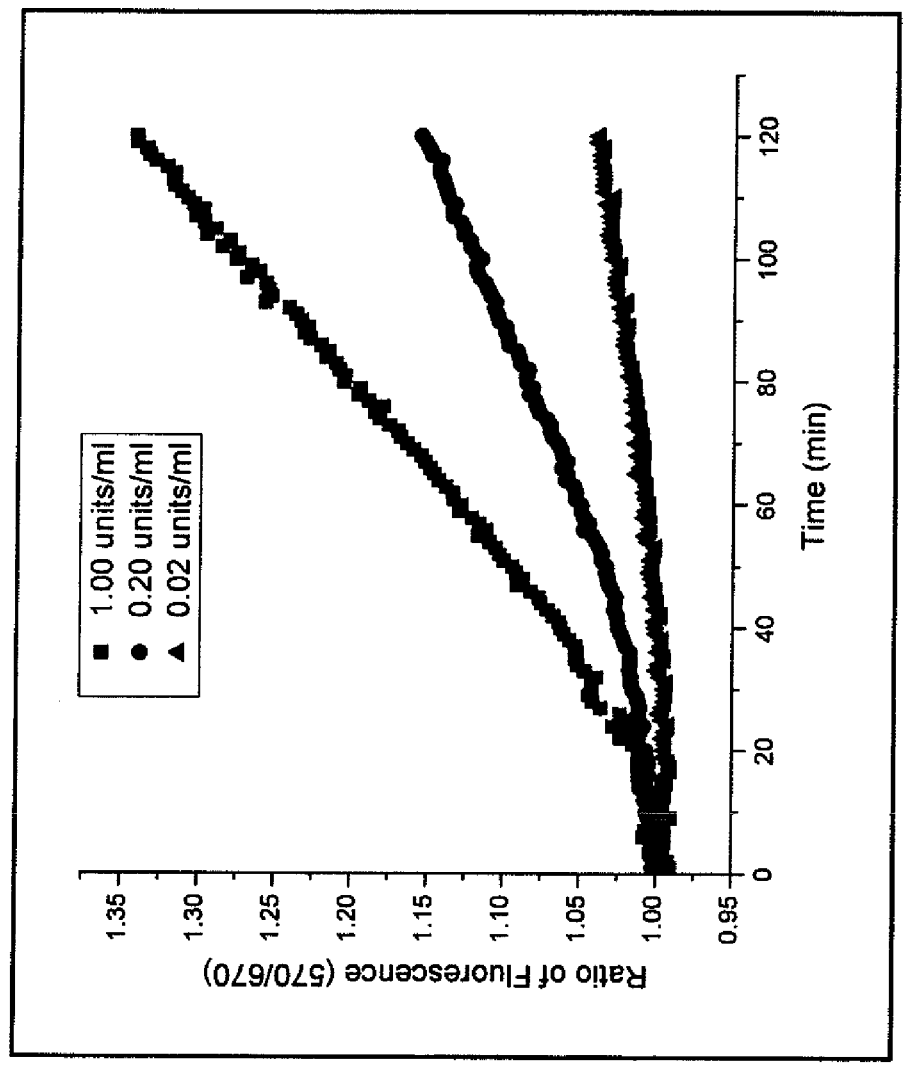
FIG. 9 presents the data from real-time monitoring of Tgase reactions using sensors in accord with one embodiment of the present invention, using 12.5 mM substrate (Z-Gln-Gly) and 1.00, 0.20, and 0.02 units/ml Transglutaminase at 30° C. Each curve represents the average reading from 5-8 reactions.
Figure 10:
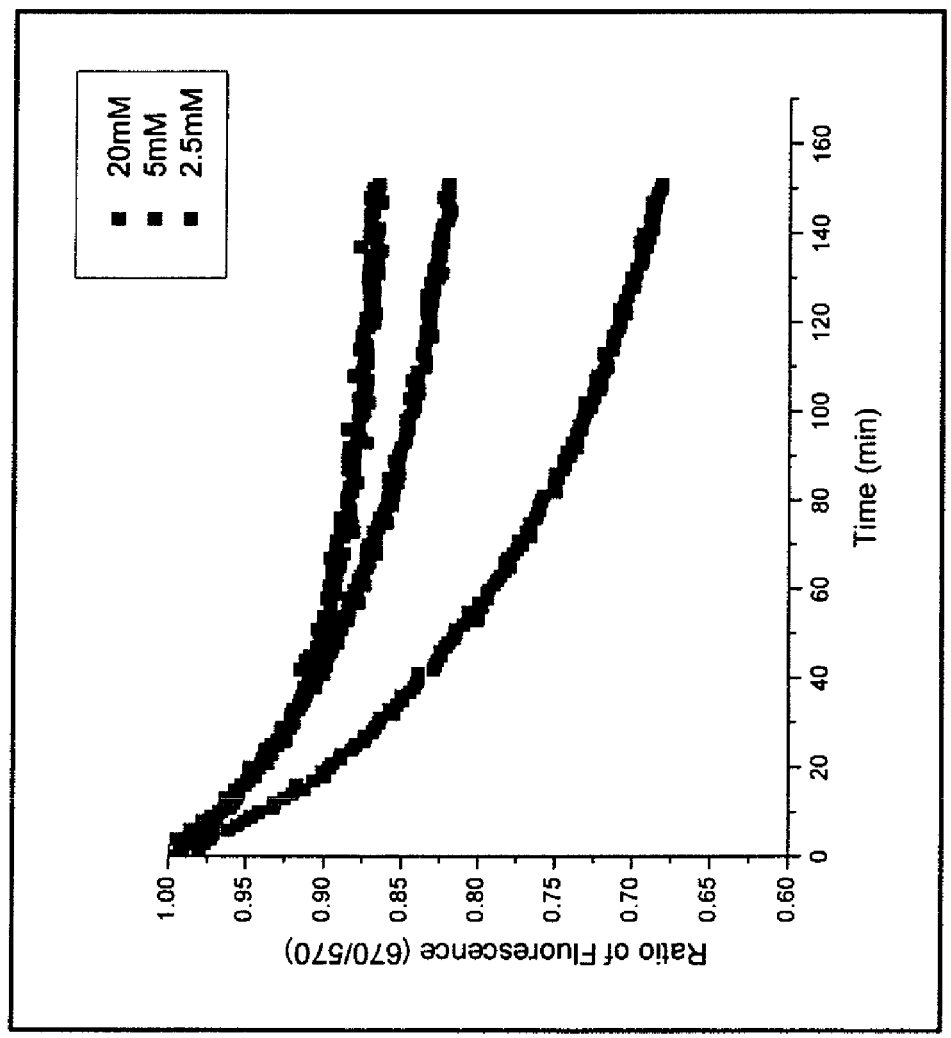
FIG. 10 presents the data from real-time monitoring of TGase reactions using sensors in accord with another embodiment of the present invention, having various substrate (Z-Gln-Gly) concentrations and 0.4 units/ml Transglutaminase at 30° C. Each curve represents the average reading from 3 reactions.

FIGS. 9 and 10 present the results of monitoring of the TGase reaction. Varying enzyme and substrate concentrations of the TGase reaction demonstrate the operation of the optical sensors. In particular, these results show that the higher the enzyme concentration or the higher the substrate concentration in the reaction, the faster ammonia is produced.

Further Applications

As discussed above, various embodiments of the present invention may be constructed to directly detect the presence of particular ions. As illustrated in Table 1 below, it is known to the art that certain diseases affect particular ion channels in a cell. Accordingly, assays for those ions utilizing the present invention may furnish a diagnostic tool to determine the presence of particular diseases. Accordingly, the scope of the present invention should be understood to also include the application of the heretofore-described subject matter to measure the ions set forth in the following tables, as well as their application to diagnose the presence of the associated diseases also appearing in the following tables.

| Channel | Gene | Channel-forming unit/ligand | OMIM | Disease |
|---|---|---|---|---|
| Cation channels: | | | | |
| CHRNA1/ACHRA | CHRNAI | α, ACh | 100690 | Myasthenia congenita |
| CHRNA4 | CHRNA4 | α, ACh | 118504 | Autosomal dominant nocturnal frontal lobe epilepsy |
| CHRNB2 | CHRNB2 | β, ACh | 118507 | Autosomal dominant nocturnal frontal lobe epilepsy |
| Polycystin-2 | PKD2 | α | 173910 | Autosomal dominant polycystic kidney disease (ADPKD) |
| CNGA3 | CNGA3 | α, cGMP | 60053 | Achromatopsia 2 (color blindness) |
| CNGB1 | CNGB1 | β, cGMP | 600724 | Autosomal recessive retinitis pigmentosa |
| CNGB3 | CNGB3 | β, cGMP | 605080 | Achromatopsia 3 |
| Sodium channels: | | | | |
| Na.1.1 | SCN1A | α | 182389 | Generalized epilepsy with febrile seizures (GEFS+) |
| Na.1.2 | SCN2A | α | 182390 | Generalized epilepsy with febrile and afebrile seizures) |
| Na.1.4 | SCN4A | α | 603967 | Paramyotonia congenital, potassium aggressive myotonia, hyperkalemic periodic paralysis |
| Na.1.5 | SCN5a | α | 600163 | Long-QT syndrome, progressive familial heart block type 1, Brugada syndrome (idiopathic ventricular arrhythmia) |
| SCNIB | SCN1B | β | 600235 | Generalized epilepsy with febrile seizures (GEFS+) |
| ENaCα | SCNNIA | α | 600228 | Pseudohypoaldosteronism type 1 (PHA1) |
| ENaCβ | SCNN1B | β | 600760 | PHA1, Liddle syndrome (dominant hypertension |
| ENaCγ | SCNN1G | γ | 600761 | PHA1, Liddle syndrome |
| Potassium channels: | | | | |
| K, 1.1. | KCNA1 | α | 176260 | Episodic ataxia with myokymia |
| KCNQI/K, LQT1 | KCNQ1 | α | 192500 | Autosomal dominant long-QT syndrome (Romano-Ward) Autosomal recessive long-QT syndrome with deafness (Jervell-Lange-Nielsen) |
| KCNQ2 | KCNQ2 | α | 602235 | BFNC (epilepsy), also with myokymia |
| KCNQ3 | KCNQ3 | α | 602232 | BFNC (epilepsy) |
| KCNO4 | KCNQ4 | α | 603537 | DFNA2 (dominant hearing loss) |
| HERG/KCNH2 | KCNH2 | α | 152427 | Long-QT syndrome |
| Kir1.1/ROMK | KCNJ1 | α | 600359 | Bartter syndrome (renal salt loss, hypokalemic alkalosis) |
| Kir2.1/IRK/KCNJ2 | KCNJ2 | α | 600681 | Long-QT syndrome with dysmorphic features (Andersen syndrome) |
| Kir6.2/KATATP$_{ATP}$ | KCNJ11 | α | 600937 | Persistent hyperinsulinemic hypoglycemia of infancy (PHHI) |
| SURI | SURI | β | 600509 | PHHI |
| KCNE1/Mink/ISK | KCNE1 | β | 176261 | Autosomal dominant long-QT syndrome (Romano-Ward) Autosomal recessive long-QT syndrome with deafness (Jervell-Lange-Nielson) |
| KCNE2/MiRP1 | KCNE2 | β | 603796 | Long-QT syndrome |
| KCNE3/MiRP2 | KCNE3 | β | 604433 | Periodic paralysis |
| Calcium channels: | | | | |
| Ca, 1.1 | CACNA1S | α | 114208 | Hypokalemic periodic paralysis, malignant hyperthermia |
| Ca, 1.4 | CACNA1F | α | 300110 | X-linked congenital stationary night blindness |
| Ca, 2.1 | CACNA1A | α | 601011 | Familial hemiplegic migraine, episodic staxia, spinocerebella ataxia type 6 |
| RyRI | RYR1 | α | 180901 | Malignant hyperthermia, central core disease |
| RyR2 | RYR2 | α | 180902 | Catecholaminergic polymorphic ventricular tachycardia, arrhythmogenic right ventricular dysplasia type 2 |
| Chloride channels: | | | | |
| CFTR | ABCC7 | α | 602421 | Cystic fibrosis, congenital bilateral asplasia of vas deference |
| ClC-1 | CLCN1 | α | 118425 | Autosomal recessive (Becker) or dominant (Thomsen myotonia |
| ClC-5 | CLCN5 | α | 300008 | Dent's disease (X-linked proteinuria and kidney stones) |
| ClC-7 | CLCN7 | α | 602727 | Osteopetrosis (recessive or dominant) |
| ClC-Kb | CLCNKB | α | 602023 | Bartter syndrome type III |
| Barttin | BSND | β | 606412 | Bartter syndrome type IV (associated with sensorineural deafness) |
| GLRA1 | GLRA1 | α, glycine | 138491 | Hyperekplexin (startle disease) |
| GABAα1 | GABRA1 | α GABA | 137160 | Juvenile myoclonus epilepsy |
| GABAγ2 | GABRG2 | γ, GABA | 137164 | Epilepsy |
| Gap junction channels: | | | | |
| Cx26 | GJB2 | | 121011 | DFNB3 (autosomal dominant hearing loss) DFNB1 (autosomal recessive hearing loss) |
| Cx30 | GJB4 | | 605425 | DFNA3 |
| Cx31 | GJB3 | | 603324 | DFNA2 |
| Cx32 | GJB1 | | 304040 | CMTX (X-linked Charcot-Mari-Tooth neuropathy) |
| AChR α7 | | | | Inflammation |
| ClC7 | | | | Osteoporosis |
| Ether-a-go-go (eag, erg, elk) | | | | Cancer |
| Gardos channel | | | | Sickle cell anemia |
| P2X7 | | | | Immune disorders |
| TRPC6 | | | | Asthma, COPD |
| TRPM1 | | | | Melanoma |
| TRPM2 | | | | Asthma |
| TRPM4 | | | | Immune disorders |

-continued

| Channel | Gene | Channel-forming unit/ligand | OMIM | Disease |
|---|---|---|---|---|
| TRPM7 | | | | Stroke |
| TRPM8 | | | | Prostate cancer |
| TRPV1 | | | | Urinary incontinence, pain |

The third column classifies channel proteins into α, β, and γ subunits, where α subunits are always directly involved in pore formation, Several β subunits are only accessory (i.e., do not form pores), as is the case, for example, with SCN1B and barttin. Others (e.g. of ENaC and GABA receptors) participate in pore formation. For ligand-gated channels, the ligand is given. Note that GABA and glycine act from the extracellular side, whereas cGMP is an intracellular messenger.

| Gene | Accession ID | Gene Locus | | Tissue Expression |
|---|---|---|---|---|
| | | | Sodium Channel Type/Disease | |
| SCN1A | GDB: 118870 S71446 | 2q24 | SCN1, vg type 1, α-subunit (280 KDa) | Brain |
| SCN1B | GDB: 127281 U12188-12104 L16242, L10338 | 19q13.1 | Hs.89634, vg type 1 $β_1$ subunit (38 KDa) | Brain, heart, skeletal muscle |
| SCN2A1 | GDB: 120367 | 2q23 | SCN2A, HBSCI, vg type II, $α_1$-subunit (280(KDa) | Brain, peripheral nerve |
| SCN2A2 | CDB: 133727 | 2q23-24.1 | HBSCH, vg type II, $α_2$-subunit vg type II, $β_2$-subunit (33 KDa) | Brain |
| SCN2B | GDB: 118871 AF019498 | | | |
| SCN3A | GDB: 132151 S69887 | 2q24-31 | vg type III, α-subunit (280 kDa) | Brain |
| SCN4A | GDB: 125181 L04216-L04236 | 17q23.1-25.3 | SkM1, vg type IV α-subunit (260 kDa), hyperkalemic periodic paralysis, paramyotonia congentia, potasstum-aggravated myotonia | Skeletal muscle |
| SCN4B | GDB: 125182 | 3q21 | vg type IV, β-subunit, | Heart, fetal skeletal muscle |
| SCN5A | GDB: 132152 | | SkM2, hH1, vg type V, α-subunit, long Q-T syndrome 3 | |
| SCN6A | GDB: 132153 | 2q21-23 | Hs99945, vg type VI, α-subunit | Heart, uterus, fetal and denervated skeletal muscle |
| SCN7A | GDB: 228137 | 12q13 | vg type VII, α-subunit | Brain, spinal cord |
| SCN8A | GDB: 631695 | | vg type VIII, α-subunit, motor end-plate disease + ataxia in mice | |
| SCN9A | GDB: 3750013 | | vg type IX, α-subunit neuroendocrine type | Thyroid and adrenal gland |
| SCN10A | GDB: 750014 | 1pter-p36.3 | hPN3, vg type X | Sensory neurons, dorsal root ganglia |
| SCNN1A | GDB: 366596 Z92978 | 12pt3 | SCNN1, nvg type 1 α-subunit of ENaC | Kidney, lung colon |
| SCNN1B | GDB: 434471 | 16p12.2-p12.1 | nvg 1 β-subunit, Liddle's syndrome, pseudohypoaldosterontsm I | Kidney, lung colon |
| SCNN1D | GDB: 6053678 | 1p36.3-p36.2 | DnaCh, nvg 1 δ-subunit | Kidney, lung, colon |
| SCNN1G | GDB: 568769 X87160 U53835-53853 | 16p122-p12.1 | nvg 1 γ-subunit, Liddle's syndrome, pseudohypoaldosterontsm I | Kidney, lung, colon |
| | | | Calcium Channel Type/Disease | |
| CACNA1A CACNL1A4 | GDB: 126432 Z80114-Z80155, X99697, U79666 | 19p13 19p13.1 | P/Q type $α_{1A}$-subunit, eqisodic ataxia 2, familial hemiplegic migraine, spinocerebellar ataxia 6; tottering, leaner, and rolling mice | Brain (cortex, bulbus, olfacorius, hippocarnpus, cerebellum, brain stem), motoneurons, kidney |
| CACNA1B CACNL1A5 | GDB: 580689 M94172, M94173 | 9q34 | CACNN, N-type $α_{1A}$-subunit | Central, peripheral nervous system |
| CACNA1C CACNL1A1 | GDB: 126094 L29636, L29634, L29629 | 12p13 12p13.3 | CCHL1A1, L-type $α_{1A}$-subunit | Heart, fibroblasts, lung, smooth muscle (2 splice variants) |
| CACNA1D CACNL1A2 | GDB: 128872 | 3p14.3 3p21.3.2? | CCHL1A2, L-type $α_{1D}$-subunit | Brain, pancreas, neuroendocrine |
| CACNA1E CACNL1A6 | GDB: 434408 | 1q25-31 | R-type $α_{1C}$-subunit | Brain, skeletal muscle (end plate) |
| CACNA1F | GDB: 6053864 | Xp11.23-11.22 | $α_{1F}$-Subunit | Retina |
| CACNIAG | AF27964 | 17q22 | T-type $α_{1G}$-subunit | Brain |
| CACNA1S CACNL1A8 | GDB: 126431 Z22672, L33798 U30666-U30707 | 1q31-32 | L-type $α_{1B}$-subunit (5% 212, 95% 190 kDa), malignant hyperthermia 5, hypokalernic periodic paralysis | Skeletal muscle (brain, kidney) |
| CACNA2 CACNL2A | GDB: 132010 Z28613, Z28609 Z28605, Z28602 Z28699, M76559 | 7q21-22 | CACNA2, CACNA2D1, $α_{g8}$-subunit (175 kDa), MHS3 | $α_{2A}$; skeletal muscle, heart, brain, ileum; $α_{2B}$; brain; $α_{2CVD}$; aorta |

-continued

| Gene | Accession ID | Gene Locus | | Tissue Expression |
|---|---|---|---|---|
| CACNB1 | GDB: 132012 | 17q21-22 | $\beta_1$-Subunit (524 aa, 54 kDa) | $\beta_1$A/M; skeletal muscle |
| CACNLB1 | GDB: 1073281 | | | $\beta_1$B/C; brain, heart, |
| | U86952-U86961 | | | spleen |
| | M76560, L06111 | | | |
| | GDB: 193328 | | | |
| CACNB2 | GDB: 132014 | 10p12 | MYSB, $\beta_2$-subunit | $\beta_2$A/B/E; brain, heart, |
| CACNLB2 | Q08289 | | | lung, aorta |
| CACNB3 | GDB: 341023 | 12q13 | $\beta_2$-subunit (482 aa) | Brain, heart, lung, spleen, |
| CACNLB3 | L27584 | | | skeletal and smooth |
| | | | | muscle, aorta, trachea, |
| | | | | ovary, colon |
| CACNB4 | GDB: 6028693 | 2q22-23 | $\beta_2$-subunit, lethargic mice | Brain, kidney |
| CACNG | GDB: 132015 | 17q24 | $\gamma$-Subunit (222 aa, 30 kDa) | Skeletal muscle, lung |
| CACNLG | L07738 | | | |
| CACNG2 | | | $\gamma$2-Subunit, stargazin, absence | Brain |
| | | | epilepsy stargazer, waggler mice | |
| RYR1 | GDB: 120359 | 19q13.1 | Ryanodine receptor 1, Ca release | Skeletal muscle, testis, |
| | | | channel, 3 splice variants, | brain, submaxillary and |
| | | | malignant hyperthermia 1, central | adrenal glands, spleen |
| | | | core disease | |
| RYR2 | GDB: 125278 | 1pter-qter | RYR2, calcium release channel | Heart, smooth muscle |
| | | 1q42.1-43 | | |
| RYR3 | GDB: 138451 | 15q14 | RYR3, calcium release channel | Brain, neonatal skeletal |
| | | 15q14-15 | | muscle, adult diaphragm |
| | | | Potassium Channel Type/Disease | |
| KCNA1 | GDB: 127903 | 12p13 | RBK1, HUK1, MBK1, AEMK, | Brain, nerve, heart, |
| | LO2750 | | Kv1.1, Shaker homolog 1, Shaker, | skeletal muscle, retina, |
| | | | episodic ataxia 1 (with myokymia) | pancreatic islet |
| KCNA1B | | 3q26.1 | Kv$\beta$1.1, Kv$\beta$1.3 (splice product), | |
| | | | $\beta$-subunit | |
| KCNA2 | GDB: 128062 | 12pter-qter | HK4, Kv1.2, Shaker homolog 2 | Brain, nerve, heart, |
| | X17622 | | | pancreatic islet |
| KCNA2B | | 1p36.3 | Kv$\beta$1.2, $\beta$-subunit | |
| KCNA8 | GDB: 128079 | 1p13.3 | Hs.1750, MK3, HLK3, HPCN3, | Skeletal muscle, |
| | L23499 | | Kv1.3, Shaker homolog 3 | lymphocytes (brain, |
| | | | | lung, thymus, spleen) |
| KCNA4 | GDB: 126730 | 11p14 | Hs.89647, Hs.1854, HK1, HPCN2, | Brain, nerve, heart, fetal |
| | M60450 | | Kv1.4, Shaker homolog 4 | skeletal muscle, |
| | M55514 | | | pancreatic islet |
| KCNA4L | GDB: 386059 | 11q14 | Shaker homolog type 4-like | |
| KCNA5 | GDB: 127904 | 12p13.3-13.2 | Hs.89509, HK2, HPCNI, Kv1.5 | Brain, heart, kidney, lung, |
| | M83254 | 12p13 | Shaker homolog 5 | skeletal muscle, |
| | M60451 | 12p13.33-12.31 | | pancreatic islet |
| KCNA6 | GDB: 128080 | 12p13 | HBK2, Kv1.6, Shaker homolog 6 | Brain, pancreatic islet |
| | X17622 | | | |
| KCNA7 | GDB: 127905 | 19q13.3 | HAK6, Kv1.7 Shaker homolog 7 | |
| KCNA8 | | | see KCNQ1 | |
| KCNA9 | | | see KCNQ1 | |
| KCNA10 | GDB: 5885822 | | Shaker homolog type 10, cGMP | |
| | | | activated | |
| KCNB1 | GDB: 128081 | 20q13.2 | Kv2.1, Shab homolog 1 | Brain, heart, kidney, |
| | | | | retina, skeletal muscle |
| KCNB2 | | | Kv2.2, Shab homolog 2 | Brain, heart, retina |
| KCNC1 | GDB: 128082 | 11p15.1 | Kv3.1, Shaw homolog 1 | Brain, skeletal muscle, |
| | S56770 | | | spleen, lymphocytes |
| | M96747 | | | |
| KCNC2 | GDB: 127906 | 19q13.3-13.4 | Kv3.2, Shaw homolog 2 | Brain |
| KCNC3 | GDB: 127907 | 19q13.3 | Kv3.3, Shaw homolog 3 | Brain, liver |
| KCNC4 | GDB: 127908 | 1p21 | Kv3.4, HKSHIIIC, Shaw homolog 4 | Brain, skeletal muscle |
| KCND1 | GDB: 128083 | | Kv4.1, Shal hormolog 1 | Brain |
| KCND2 | GDB: 134771 | | RK5, Kv4.2, Shal homolog 2 | Brain, heart, aorta |
| KCND3 | GDB: 134772 | | Kv4.3, KSHIVB, Shal homolog 3 | |
| KCNE1 | GDB: 127909 | 21q22.1-22.2 | MinK, ISK, vg Isk homolog 1 (129 | Kidney, submandibular |
| | | | aa), long Q-T syndrome 5 | gland, uterus, heart, |
| | | | | cochlea, retina |
| KCNMA1 | GDB: 386031 | 10pter-qter | SLO, Hs.62679, $\alpha$-subunit member | Fetal skeletal muscle |
| | U09383-4 | 7q32.1 | 1, $\alpha$-subunit of maxiK or BK | |
| | U02632 | | channel | |
| KCNMB1 | GDB: 6099615 | 5q34 | hSLO-$\beta$, $\beta$-subunit member 1 (191 | Smooth, fetal skeletal |
| | U42600 | | aa), $\beta$-subunit of max1K or BK | muscle, brain |
| | | | channel | (hippocampus, corpus |
| | | | | callosum) |
| KCNN1 | U69883 | | SK(Ca)1, small-conductance Ca- | Brain, heart |
| | | | activated K channel, apamin- | |
| | | | insensitive | |
| KCNN2 | | | SK(Ca)2, apamin sensitive | Brain, adrenal gland |

-continued

| Gene | Accession ID | Gene Locus | | Tissue Expression |
|---|---|---|---|---|
| KCNN3 | Y08263 AA285078 | 1q? | SK(Ca)3, small-conductance Ca-activated K channel, intermediate apamin sensitivity | Brain, heart, (human embryonic) skeletal muscle, liver |
| KCNN4 | AF022150 AF022797 AF033021 AF000972 | 19q13.2 | IK1, intermediate-conductance Ca-activated K channel, KCa4, SK4, Gantos channel | T lymphocytes, colon, smooth muscles, prostata, red blood cells, neurons |
| KCNQ1 | GDB: 741244 U40990 | 11p15.5 | KCNA9, (KV)LQT1, KQT-like subfamily member 1, long Q-T syndrome 1 | Heart, cochlea, kidney, lung, placenta, colon |
| KCNQ2 | GDB: 9787229, Y15065, AF033348 | 20q13.3 | KQT-like subfamily member 2 (872 aa) | Brain |
| KCNQ3 | GDB: 9787230 AF033347 | 8q24.22-24.3 | KQT-like subfamily member 3 (825 aa) | Brain |
| HERG | GDB: 407638 | 7q35-36 | HERG, similar to ether-a-go go (eag), IKr, long Q-T syndrome 2 | Brain, heart |
| KCNJ1 | GDB: 204206 U65406, U12541 | 11q24 | ROMK1, Kir1.1, Hs.463, Bartter/hyperprostaglandin E syndrome | Kidney, pancreatic islets |
| KCNJ2 | GDB: 278964 U12507 | 17pter-qter | IRK1, Kir2.1, Hs.1547 | Muscle, neural tissue, heart |
| KCNJ3 | GDB: 278325 U50964 | 2q24.1 | GIRK1, Kir3.1 | Heart, cerebellum |
| KCNJ4 | GDB: 374080 Z97056 | 22q13.1 | HIR, HIRK1, HIRK2, Kir2.3 | Heart, skeletal muscle, brain |
| KCNJ5 | GDB: 547948 | 11q24 | CIR, KATP1, GIRK4, Kir3.4 | Heart, pancreas |
| KCNJ6 | GDB: 547949 U24660 | 21q22.1 | KCNJ7, GIRK2, KATP2, BIR1, Kir3.2, ataxia, weaver mice | Cerebellum, pancreatic islet |
| KCNJ8 | GDB: 633096 | 12p11.23] | Kir6.1, uKATP, ubiquitous $K_{ATP}$ α-subunit | Brain, heart, skeletal, smooth muscle, others |
| KCNJ10 | GDB: 3750203 | 1q22-23] | Kir1.2, Kir4.1 | Glia |
| KCNJ11 | GDB: 7009893 | [11p15.1] | Kir6.2, BIR, K(ATP) α-subunit, hyperinsulinemic hypoglycemia | Pancreatic islets |
| KCNJ12 | GDB: 4583927 | [17p11.1] | Kir2.2 | |
| KCNJ15 | GDB: 6275865 | [21q22.2] | Kir4.2 | |
| KCNJN1 | GDB: 6108062 | [ ] | Kir2.2v, subfamily inhibitor 1 | |
| SUR1 | GDB: 591970 | [11p15.1] | SUR(1), sulfonylurea receptor, K(ATP) β-subunit, hyperinsulinemic hypoglycemia | Pancreatic islets |
| SUR2 | | 12p12.1] | SUR2, SUR2A, B, sulfonylurea receptor 2 (1545-aa), β-subunit of K(ATP) | 2A: heart, 2B: brain, liver, skeletal, smooth muscle, urinary bladder |
| KCNK1 | GDB: 6045446 | 1q42-43 | DPK, TWIK1 | Kidney |
| KCNK2 | | 1q41 | TREK1 | Brain |
| KCNK3 | GDB: 9773281 | 2p23 | TASK | Kidney |

| Therapeutic Target | Enzyme Family | Assay |
|---|---|---|
| Alzheimer's | CMGC | ERK2 (P42mapk) |
| Alzheimer's | Phospholipase | PLA2 |
| Alzheimer's | Cyclooxygenases | COX2 |
| Alzheimer's | CaMK | MARK1 |
| Alzheimer's | CaMK | MARK2 |
| Alzheimer's | AGC | PKCalpha |
| Alzheimer's | AGC | PKCgamma |
| Alzheimer's | AGC | PKCgamma |
| Alzheimer's | Cysteine proteases | caspase-3 |
| Alzheimer's | Cysteine proteases | caspase-6 |
| Alzheimer's | Aspartic proteases | BACE-1 (beta-secretase) |
| Alzheimer's | Aspartic proteases | cathepsin D |
| Alzheimer's | Aspartic proteases | cathepsin F |
| Alzheimer's | Metalloproteases | ACE |
| Alzheimer's | Metalloproteases | ACE |
| Alzheimer's | Metalloproteases | TACE |
| Alzheimer's | NO synthases | constitutive NOS (cerebellar) |
| Alzheimer's | Monoamine & neurotransmitter synthesis & metabolism | acetylcholinesterase |
| Alzheimer's | Monoamine & neurotransmitter synthesis & metabolism | COMT (catechol-O-methyl transferase) |
| Alzheimer's | Monoamine & neurotransmitter synthesis & metabolism | MAO-A |

-continued

| Therapeutic Target | Enzyme Family | Assay |
| --- | --- | --- |
| Alzheimer's | Monoamine & neurotransmitter synthesis & metabolism | MAO-B |
| Alzheimer's | Monoamine & neurotransmitter synthesis & metabolism | tyrosine hydroxylase |
| Alzheimer's | Phospholipase C | PLC |
| Alzheimer's | Miscellaneous enzymes | xanthine oxidase/superoxide O2-scavenging |
| Dependence/Addiction | AGC | PKA |
| Dependence/Addiction | AGC | PKCalpha |
| Dependence/Addiction | AGC | PKCbeta 1 |
| Dependence/Addiction | AGC | PKCbeta 2 |
| Dependence/Addiction | AGC | PKCdelta |
| Dependence/Addiction | Monoamine & neurotransmitter synthesis & metabolism | GABA transaminase |
| Dependence/Addiction | Cyclases | adenylyl cyclase (stimulated) |
| Dependence/Addiction | Phospholipase C | PLC |
| Dependence/Addiction | ATPase | ATPase (Na+/K+) |
| Inflammation/Arthritis/Allergy | RTK | EGFR kinase |
| Inflammation/Arthritis/Allergy | RTK | FLT-1 kinase (VEGFR1) |
| Inflammation/Arthritis/Allergy | RTK | KDR kinase (VEGFR2) |
| Inflammation/Arthritis/Allergy | CTK | Fyn kinase |
| Inflammation/Arthritis/Allergy | CTK | HCK |
| Inflammation/Arthritis/Allergy | CTK | Lck kinase |
| Inflammation/Arthritis/Allergy | CTK | Lyn kinase |
| Inflammation/Arthritis/Allergy | CTK | ZAP70 kinase |
| Inflammation/Arthritis/Allergy | CMGC | ERK2 (P42mapk) |
| Inflammation/Arthritis/Allergy | CMGC | JNK 1 |
| Inflammation/Arthritis/Allergy | CMGC | JNK 2 |
| Inflammation/Arthritis/Allergy | CMGC | P38alpha kinase |
| Inflammation/Arthritis/Allergy | Phospholipase | PLA2 |
| Inflammation/Arthritis/Allergy | Cyclooxygenases | COX1 |
| Inflammation/Arthritis/Allergy | Cyclooxygenases | COX2 |
| Inflammation/Arthritis/Allergy | TXA2 synthetase | TXA2 synthetase |
| Inflammation/Arthritis/Allergy | CaMK | MAPKAPK2 |
| Inflammation/Arthritis/Allergy | AGC | PKA |
| Inflammation/Arthritis/Allergy | Lipoxygenases | 12-lipoxygenase |
| Inflammation/Arthritis/Allergy | Lipoxygenases | 15-lipoxygenase |
| Inflammation/Arthritis/Allergy | Serine proteases | elastase |
| Inflammation/Arthritis/Allergy | Serine proteases | cathepsin G |
| Inflammation/Arthritis/Allergy | Serine proteases | kallikrein |
| Inflammation/Arthritis/Allergy | Serine proteases | tryptase |
| Inflammation/Arthritis/Allergy | Cysteine proteases | caspase-1 |
| Inflammation/Arthritis/Allergy | Cysteine proteases | caspase-4 |
| Inflammation/Arthritis/Allergy | Cysteine proteases | caspase-5 |
| Inflammation/Arthritis/Allergy | Cysteine proteases | cathepsin B |
| Inflammation/Arthritis/Allergy | Cysteine proteases | cathepsin X |
| Inflammation/Arthritis/Allergy | Aspartic proteases | cathepsin F |
| Inflammation/Arthritis/Allergy | Metalloproteases | MMP-1 |
| Inflammation/Arthritis/Allergy | Metalloproteases | MMP-2 |
| Inflammation/Arthritis/Allergy | Metalloproteases | MMP-3 |
| Inflammation/Arthritis/Allergy | Metalloproteases | MMP-7 |
| Inflammation/Arthritis/Allergy | Metalloproteases | MMP-8 |
| Inflammation/Arthritis/Allergy | Metalloproteases | MMP-9 |
| Inflammation/Arthritis/Allergy | Metalloproteases | MMP-13 |
| Inflammation/Arthritis/Allergy | Metalloproteases | MT1-MMP (MMP-14) |
| Inflammation/Arthritis/Allergy | Metalloproteases | TACE |
| Inflammation/Arthritis/Allergy | Phosphatases | phosphatase CD45 |
| Inflammation/Arthritis/Allergy | Phosphodiesterases | PDE2 |
| Inflammation/Arthritis/Allergy | Phosphodiesterases | PDE4 |
| Inflammation/Arthritis/Allergy | Phosphodiesterases | acid sphingomyelinase |
| Inflammation/Arthritis/Allergy | Monoamine & neurotransmitter synthesis & metabolism | HNMT (histamine N-methyltransferase) |
| Inflammation/Arthritis/Allergy | Miscellaneous enzymes | myeloperoxidase |
| Inflammation/Arthritis/Allergy | Miscellaneous enzymes | xanthine oxidase/superoxide O2-scavenging |
| Neuroprotection | RTK | TRKB |
| Neuroprotection | CMGC | CDK5 |
| Neuroprotection | CMGC | DYRK1a |
| Neuroprotection | CMGC | ERK1 |
| Neuroprotection | CMGC | ERK2 (P42mapk) |
| Neuroprotection | MCGC | JCK 3 |
| Neuroprotection | Cyclooxygenases | COX1 |
| Neuroprotection | Cyclooxygenases | COX2 |
| Neuroprotection | CaMK | CaMK2alpha |
| Neuroprotection | AGC | PKA |
| Neuroprotection | Cysteine proteases | caspase-3 |
| Neuroprotection | Phosphodiesterases | PDE1 |
| Neuroprotection | Phosphodiesterases | PDE6 |
| Neuroprotection | NO synthases | constitutive NOS (endothelial) |
| Neuroprotection | NO synthases | constitutive NOS (cerebellar) |

-continued

| Therapeutic Target | Enzyme Family | Assay |
|---|---|---|
| Neuroprotection | Monoamine & neurotransmitter syntheses & metabolism | acetylcholinesterase |
| Neuroprotection | Monoamine & neurotransmitter syntheses & metabolism | COMT (catechol-O-methyl transferase) |
| Neuroprotection | Monoamine & neurotransmitter syntheses & metabolism | GABA transaminase |
| Neuroprotection | Monoamine & neurotransmitter syntheses & metabolism | HNMT (histamine N-methyltransferase) |
| Neuroprotection | Monoamine & neurotransmitter syntheses & metabolism | MAO-A |
| Neuroprotection | Monoamine & neurotransmitter syntheses & metabolism | MAO-A |
| Neuroprotection | Monoamine & neurotransmitter syntheses & metabolism | PNMT (phenylethanoiamine-N-methyl transferase) |
| Neuroprotection | Monoamine & neurotransmitter syntheses & metabolism | tyrosine hydroxylase |
| Neuroprotection | Cyclases | guanylyl cyclase (basal) |
| Neuroprotection | Cyclases | guanylyl cyclase (stimulated) |
| Neuroprotection | ATPase | ATPase (Na+/K+) |
| Neuroprotection | Miscellaneous enzymes | xanthine oxidase/superoxide O2-scavenging |
| Parkinson | CMGC | JNK 1 |
| Parkinson | Phospholipase | PLA2 |
| Parkinson | Cyclooxygenases | COX2 |
| Parkinson | Cysteine proteases | caspase-3 |
| Parkinson | NO synthases | constitutive NOS (cerebellar) |
| Parkinson | Monoamine & neurotransmitter syntheses & metabolism | acetylcholinesterase |
| Parkinson | Monoamine & neurotransmitter syntheses & metabolism | COMT (catechol-O-methyl transferase) |
| Parkinson | Monoamine & neurotransmitter syntheses & metabolism | MAO-A |
| Parkinson | Monoamine & neurotransmitter syntheses & metabolism | MAO-B |
| Cancer | RTK | Axl kinase |
| Cancer | RTK | c-kit kinase |
| Cancer | RTK | c-kit kinase |
| Cancer | RTK | EGFR kinase |
| Cancer | RTK | EphA1 kinase |
| Cancer | RTK | EphA3 kinase |
| Cancer | RTK | EphA4 kinase |
| Cancer | RTK | EphB2 kinase |
| Cancer | RTK | FGFR1 kinase |
| Cancer | RTK | FGFR2 kinase |
| Cancer | RTK | FGFR3 kinase |
| Cancer | RTK | FGFR4 kinase |
| Cancer | RTK | FLT-1 kinase (VEGFR1) |
| Cancer | RTK | FLT-3 kinase |
| Cancer | RTK | FLT-4 kinase (VEGFR3) |
| Cancer | RTK | Fms/CSFR kinase |
| Cancer | RTK | HER2/ErbB2 kinase |
| Cancer | RTK | HER4/ErbB4 kinase |
| Cancer | RTK | KDR kinase (VEGFR2) |
| Cancer | RTK | PDGFRalpha kinase |
| Cancer | RTK | PDGFRbeta kinase |
| Cancer | RTK | Ret kinase |
| Cancer | RTK | TIE2 kinase |
| Cancer | RTK | TRKA |
| Cancer | CTK | Abl kinase |
| Cancer | CTK | BLK |
| Cancer | CTK | BMX (Bk) kinase |
| Cancer | CTK | BRK |
| Cancer | CTK | BTK |
| Cancer | CTK | CSK |
| Cancer | CTK | FAK |
| Cancer | CTK | Fes kinase |
| Cancer | CTK | Fyn kinase |
| Cancer | CTK | JAK2 |
| Cancer | CTK | JAK3 |
| Cancer | CTK | Lck kinase |
| Cancer | CTK | PYK2 |
| Cancer | CTK | Src kinase |
| Cancer | CTK | Syk |
| Cancer | CTK | Yes kinase |
| Cancer | CMGC | CDC2/CDK1 (cycB) |
| Cancer | CMGC | CDK2 (cycE) |
| Cancer | CMGC | CDK4 (cycD1) |
| Cancer | CMGC | CDK5 |
| Cancer | CMGC | CK2 (casein kinase 2) |

| Therapeutic Target | Enzyme Family | Assay |
| --- | --- | --- |
| Cancer | CMGC | DYRK1a |
| Cancer | CMGC | ERK1 |
| Cancer | CMGC | ERK2 (P42mapk) |
| Cancer | CMGC | HIPK2 |
| Cancer | CMGC | IKKalpha |
| Cancer | CMGC | IKKbeta |
| Cancer | CMGC | JNK 1 |
| Cancer | CMGC | JNK 2 |
| Cancer | CMGC | NEK1 |
| Cancer | CMGC | NEK2 |
| Cancer | CMGC | NEK4 |
| Cancer | CMGC | p38alpha kinase |
| Cancer | CMGC | p38beta 2 kinase (SAPK2b2) |
| Cancer | CMGC | p38delta kinase |
| Cancer | CMGC | p38ganuna kinase |
| Cancer | Cyclooxygenases | COX2 |
| Cancer | CaMK | CaMK1delta |
| Cancer | CaMK | CaMK |
| Cancer | CaMK | CHK1 |
| Cancer | CaMK | CHK2 |
| Cancer | CaMK | DAPK1 |
| Cancer | CaMK | DAPK2 |
| Cancer | CaMK | MAPKAPK2 |
| Cancer | CaMK | MAPKAPK3 |
| Cancer | CaMK | MAPKAPK5 (PRAK0 |
| Cancer | CaMK | MAARK1 |
| Cancer | CaMK | MARK2 |
| Cancer | CaMK | MARK4 |
| Cancer | CaMK | Pim 1 kinase |
| Cancer | CaMK | Pirn2 kinase |
| Cancer | AGC | Akt1/PKBalpha |
| Cancer | AGC | Akt2/PKBbeta |
| Cancer | AGC | Akt3/PKBgamma |
| Cancer | AGC | AurA/Aur2 kinase |
| Cancer | AGC | AurB/Aur1 kinase |
| Cancer | AGC | AurC/Aur3 kinase |
| Cancer | AGC | P70S6Ke |
| Cancer | AGC | PDK1 |
| Cancer | AGC | PKA |
| Cancer | AGC | PKCalpha |
| Cancer | AGC | PKCbeta 1 |
| Cancer | AGC | PKCbeta 2 |
| Cancer | AGC | PKCdelta |
| Cancer | AGC | PKCgamma |
| Cancer | AGC | PKG2 |
| Cancer | AGC | ROCK1 |
| Cancer | AGC | ROCK2 |
| Cancer | AGC | RSK2 |
| Cancer | AGC | SGK1 |
| Cancer | Lipoxygenases | 12-lipoxygenase |
| Cancer | TKL | RAF-1 kinase |
| Cancer | STE | MEK1/MAP2K1 |
| Cancer | STE | MKK4/JNK1 |
| Cancer | STE | MKK6 |
| Cancer | STE | PAK1 |
| Cancer | STE | PAK2 |
| Cancer | Serine proteases | elastase |
| Cancer | Serine proteases | cathepsin G |
| Cancer | Cysteine proteases | caspase-2 |
| Cancer | Cysteine proteases | caspase-3 |
| Cancer | Cysteine proteases | caspase-8 |
| Cancer | Cysteine proteases | caspase-9 |
| Cancer | Cysteine proteases | cathepin B |
| Cancer | Cysteine proteases | cathepsin H |
| Cancer | Cysteine proteases | cathepsin L |
| Cancer | Cysteine proteases | cathepsin X |
| Cancer | Aspartic proteases | cathepsin D |
| Cancer | Aspartic proteases | cathepsin E |
| Cancer | Metalloproteases | MMP-1 |
| Cancer | Metalloproteases | MMP-2 |
| Cancer | Metalloproteases | MMP-3 |
| Cancer | Metalloproteases | MMP-7 |
| Cancer | Metalloproteases | MMP-8 |
| Cancer | Metalloproteases | MMP-9 |
| Cancer | Metalloproteases | MMP-12 |
| Cancer | Metalloproteases | MMP-13 |
| Cancer | Metalloproteases | MT1-MMP (MMP-14) |
| Cancer | Metalloproteases | TACE |

-continued

| Therapeutic Target | Enzyme Family | Assay |
|---|---|---|
| Cancer' | Metalloproteases | MMP-1 |
| Cancer | Phosphatases | phosphatase 1B |
| Cancer | Phosphatases | phosphatase 2B |
| Cancer | Phosphodiesterases | PDE2 |
| Cancer | Phosphodiesterases | PDE4 |
| Cancer | Phosphodiesterases | PDE5 |
| Cancer | Phosphodiesterases | acid spingomyelinase |
| Cancer | NO synthases | constitutive NOS (endothelial) |
| Cancer | NO synthases | constitutive NOS (cerebellar) |
| Cancer | Cyclases | adenylyl cyclase (basal) |
| Cancer | Cyclases | adenylyl cyclase (stimulated) |
| Cancer | Phospholipase C | PLC |
| Cancer | Miscellaneous enzymes | myeloperoxidase |
| Cancer | Miscellaneous enzymes | xanthine oxidase/superoxide O2-scavenging |
| Diabetes | RTK | Ax1 kinase |
| Diabetes | RTK | EGFR kinase |
| Diabetes | RTK | IGFIR kinase |
| Diabetes | CMGC | ERK2 (P42mapk) |
| Diabetes | CMGC | Jnk1 |
| Diabetes | Cyclooxygenases | COX2 |
| Diabetes | TXA2 synthetase | TXA2 synthetase |
| Diabetes | CaMK | AMPKalpha |
| Diabetes | AGC | Akt1/PKBalpha |
| Diabetes | AGC | Akt2/PKBbeta |
| Diabetes | AGC | Akt3/PKBgamma |
| Diabetes | AGC | PDK1 |
| Diabetes | AGC | PKA |
| Diabetes | AGC | PKCalpha |
| Diabetes | AGC | PKCbeta 1 |
| Diabetes | AGC | PKCbeta 2 |
| Diabetes | AGC | PKCgamma |
| Diabetes | AGC | SGK2 |
| Diabetes | Metalloproteases | ACE |
| Diabetes | Metalloproteases | MMP-1 |
| Diabetes | Metalloproteases | MMP-2 |
| Diabetes | Metalloproteases | MMP-3 |
| Diabetes | Metalloproteases | MMP-7 |
| Diabetes | Metalloproteases | MMP-8 |
| Diabetes | Metalloproteases | MMP-9 |
| Diabetes | Metalloproteases | MT1-MMP (MMP-14) |
| Diabetes | Metalloproteases | TACE |
| Diabetes | Phosphodiesterases | PDE3 |
| Diabetes | Phosphodiesterases | PDE4 |
| Diabetes | Phosphodiesterases | PDE5 |
| Diabetes | NO synthases | constitutive NOS (endothelial) |
| Diabetes | Monoamine & neurotransmitter synthesis & metabolism | acetylcholinesterase |
| Diabetes | Monoamine & neurotransmitter synthesis & metabolism | GABA transaminase |
| Diabetes | Monoamine & neurotransmitter synthesis & metabolism | MAO-B |
| Diabetes | Cyclases | adenylyl cyclase (basal) |
| Diabetes | Miscellaneous enzymes | acetylCoA synthetase |
| Diabetes | Miscellaneous enzymes | HMG-CoA reductase |
| Diabetes | Miscellaneous enzymes | xanthine oxidase/superoxide O2-scavenging |
| Metabolic Diseases | Cyclooxygenases | COX2 |
| Metabolic Diseases | AGC | PKA |
| Metabolic Diseases | Metalloproteases | ACE |
| Metabolic Diseases | Phosphodiesterases | PDE3 |
| Metabolic Diseases | Phosphodiesterases | PDE4 |
| Metabolic Diseases | NO synthases | constitutive NOS (endothelial) |
| Metabolic Diseases | Miscellaneous enzymes | acetylCoA synthetase |
| Metabolic Diseases | Miscellaneous enzymes | HMG-CoA reductase |
| Metabolic Diseases | Miscellaneous enzymes | xanthine oxidase/superoxide 02-scavenging |
| Obesity | CTK | PYK2 |
| Obesity | CMGC | JNK1 |
| Obesity | CaMK | AMPJakoga |
| Obesity | AGC | PKA |
| Obesity | Metalloproteases | ACE |
| Obesity | Metalloproteases | ACE |
| Obesity | Phosphatases | phosphatase 1B |
| Obesity | Phosphodiesterases | PDE2 |
| Obesity | Phosphodiesterases | PDE3 |
| Obesity | Monoamine & neurotransmitter synthesis & metabolism | acetylcholinesterase |
| Obesity | ATPase | ATPase (Na+/K+) |
| Obesity | Miscellaneous enzymes | HMG-CoA reductase |
| Reproduction | Phospholipase | PLA2 |

-continued

| Therapeutic Target | Enzyme Family | Assay |
|---|---|---|
| Reproduction | Cyclooxygenases | COX1 |
| Reproduction | Cyclooxygenases | COX2 |
| Reproduction | Phosphodiesterases | PDE5 |
| Reproduction | NO synthases | constitutive NOS (endothelial) |
| Reproduction | Cyclases | guanylyl cyclase (stimulated) |
| Cystic Fibrosis | Phospholipase | PLA2 |
| Cystic Fibrosis | TXA2 synthetase | TXA2 synthetase |
| Cystic Fibrosis | AGC | PKA |
| Cystic Fibrosis | AGC | PKCbeta 1 |
| Cystic Fibrosis | AGC | PKCbeta 2 |
| Cystic Fibrosis | Serine proteases | elastase |
| Cystic Fibrosis | Serine proteases | cathepsin G |
| Cystic Fibrosis | Metalloproteases | MMP-2 |
| Cystic Fibrosis | Phosphodiesterases | PDE3 |
| Cystic Fibrosis | Phosphodiesterases | PDE5 |
| Cystic Fibrosis | Cyclases | adenylyl cyclase (stimulated) |
| Cystic Fibrosis | Phospholipase C | PLC |
| Cystic Fibrosis | Miscellaneous enzymes | myeloperoxidase |
| Immunosuppression Profile | RTK | EGFR kinase |
| Immunosuppression Profile | CTK | JAK3 |
| Immunosuppression Profile | CMGC | ERK2 (P42mapk) |
| Immunosuppression Profile | Cyclooxygenases | COX1 |
| Immunosuppression Profile | Cyclooxygenases | COX2 |
| Immunosuppression Profile | Serine proteases | elastase |
| Immunosuppression Profile | Serine proteases | cathepsin G |
| Immunosuppression Profile | Serine proteases | tryptase |
| Immunosuppression Profile | Cysteine proteases | cathepsin B |
| Immunosuppression Profile | Metalloproteases | ECE-1 |
| Immunosuppression Profile | Metalloproteases | ECE-1 |
| Immunosuppression Profile | Metalloproteases | MMP-1 |
| Immunosuppression Profile | Metalloproteases | MMP-2 |
| Immunosuppression Profile | Metalloproteases | MMP-9 |
| Immunosuppression Profile | Phosphatases | phosphatase CD45 |
| Immunosuppression Profile | Phosphodiesterases | PDE4 |
| Immunosuppression Profile | Phosphodiesterases | acid spingomyelinase |
| Immunosuppression Profile | Cyclases | adenylyl cyclase (basal) |
| Immunosuppression Profile | Cyclases | adenylyl cyclase (stimulated) |
| Migraine | Cyclooxygenases | COX2 |
| Migraine | NO synthases | constitutive NOS (cerebellar) |
| Migraine | Monoamine & neurotransmitter synthesis & metabolism | GABA transaminase |
| Migraine | Cyclases | guanylyl cyclase (stimulated) |
| Pain | CMGC | ERK2 (42mapk) |
| Pain | Phospholipase | PLA2 |
| Pain | Cyclooxygenases | COX1 |
| Pain | Cyclooxygenases | COX2 |
| Pain | AGC | PKA |
| Pain | Serine proteases | elastase |
| Pain | Metalloproteases | MMP-1 |
| Pain | Metalloproteases | MMP-2 |
| Pain | Metalloproteases | MMP-3 |
| Pain | Metalloproteases | MMP-7 |
| Pain | Phosphodiesterases | PDE4 |
| Pain | NO synthases | constitutive NOS (endothelial) |
| Pain | NO synthases | constitutive NOS (cerebellar) |
| Pain | Monoamine & neurotransmitter synthesis & metabolism | GABA transaminase |
| Pain | Monoamine & neurotransmitter synthesis & metabolism | MAO-A |
| Pain | Monoamine & neurotransmitter synthesis & metabolism | MAO-B |
| Pain | Monoamine & neurotransmitter synthesis & metabolism | tyrosine hydroxylase |
| Pain | Miscellaneous enzymes | xanthine oxidase/superoxide 02-scavenging |

Thus, according to various features, the systems, methods and devices of the invention provide, without limitation, a novel approach for using optodes and cells for measurement, including drug discovery and the monitoring of enzymatic reactions; the coating of an ion-selective PVC cocktail with TEFLON to prevent salt interference; an approach for using the optodes for extracellular measurement in a 96-well plate format, and for HERG and ammonia screening. The invention also provides a microdevice for combining optodes with cell measurements, sensor inserts for a well plate (such as PVC-coated glass disks), and bio-compatible coatings for optodes. Commercial applications for the invention include, without limitation, drug discovery, clinical monitoring, toxicity studies, chemical and biological detection, and the like.

Additional applications and protocols for analyzing ion-channel activity are described in U.S. Pat. No. 6,969,449, the entirety of which is incorporated by reference. Such protocols can be readily adapted for use with the optical ion sensors and cell assay systems described herein.

It will therefore be seen that the foregoing represents a highly advantageous approach to measurements using optical biosensor arrays. The terms and expressions employed herein are used as terms of description and not of limitation and there is no intention, in the use of such terms and expressions, of excluding any equivalents of the features shown and described or portions thereof, but it is recognized that various modifications are possible within the scope of the invention claimed.

What is claimed is:

1. An optode for monitoring a chemical reaction occurring within a living cell, the optode comprising an ion-selective ionophore, a source of triggering ions, and a signaling agent responsive to the triggering ions, wherein (i) the ionophore is selective for the ionic reaction product, (ii) the source of triggering ions is in communication with the ionophore such that binding of a reaction-product ion to the ionophore causes the triggering-ion source to release a triggering ion to interact with the signaling agent to produce an observable signal, and (iii) the optode has a PEG-lipid coating.

2. The optode of claim 1 wherein the optode is configured for introduction into the cell without compromising the viability of the cell.

3. The optode of claim 1 further comprising means facilitating covalent attachment of the optode to an exterior membrane of the cell.

4. The optode of claim 3 wherein the attachment-facilitating means comprises an antibody.

5. The optode of claim 1 further comprising a plasticized polymer, wherein the signaling agent comprises a chromoionophore in the polymer.

6. The optode of claim 5 wherein the polymer comprises polyvinylchloride with doctyl sebacate.

7. The optode of claim 5 wherein the chromoionophore is one or more of the group consisting of an absorbance-based pH indicator or a fluorescence based pH indicator.

8. The optode of claim 5 wherein the ionophore is a non-fluorescent ion-binder.

9. The optode of claim 5 further comprising a glass substrate.

10. The optode of claim 5 further comprising an insulative layer applied to the polymer.

11. An optical ion sensor particle comprising an ionophore, a chromoionophore, a polymer, and an additive, wherein the optical ion sensor particle is in the form of a nanosphere containing a PEG-lipid coating.

12. The optical ion sensor particle of claim 11, wherein the ionophore is Potassium Ionophore III, Sodium Ionophore IV, Sodium Ionophore V, Sodium Ionophore VI, Calcium Ionophore III, or Calcium Ionophore IV.

13. The optical ion sensor particle of claim 11, wherein the chromoionophore is Chromoionophore II or Chromoionophore III.

14. The optical ion sensor particle of claim 11, wherein the polymer is polyvinyl chloride.

15. The optical ion sensor particle of claim 11, further comprising a plasticizer.

16. The optical ion sensor particle of claim 15, wherein the plasticizer is dioctyl sebacate.

17. The optical ion sensor particle of claim 11, wherein the optical ion sensor particle comprises an ionophore, a chromoionophore, polyvinyl chloride, dioctyl sebacate, and an additive.

18. The optical ion sensor particle of claim 17, wherein the chromoionophore is Chromoionophore III.

19. The optical ion sensor particle of claim 11, wherein the PEG-lipid is DSPE-PEG 500 or DSPE-PEG (2000) Folate.

20. The optical ion sensor particle of claim 18, wherein the PEG-lipid is DSPE-PEG 500 or DSPE-PEG (2000) Folate.

* * * * *